US010493039B2

(12) United States Patent
Rotello et al.

(10) Patent No.: US 10,493,039 B2
(45) Date of Patent: Dec. 3, 2019

(54) STABILIZED POLYMERIC NANOCAPSULES, DISPERSIONS COMPRISING THE NANOCAPSULES, AND METHODS FOR THE TREATMENT OF BACTERIAL BIOFILMS

(71) Applicant: THE UNIVERSITY OF MASSACHUSETTS, Boston, MA (US)

(72) Inventors: Vincent M. Rotello, Amherst, MA (US); Ryan Francis Landis, Amherst, MA (US); Akash Gupta, Amherst, MA (US); Yiwei Lee, Amherst, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/757,092

(22) PCT Filed: Aug. 16, 2016

(86) PCT No.: PCT/US2016/047134
§ 371 (c)(1),
(2) Date: Mar. 2, 2018

(87) PCT Pub. No.: WO2017/040024
PCT Pub. Date: Mar. 9, 2017

(65) Prior Publication Data
US 2018/0177738 A1 Jun. 28, 2018

Related U.S. Application Data

(60) Provisional application No. 62/213,779, filed on Sep. 3, 2015.

(51) Int. Cl.
*A61K 9/107* (2006.01)
*A61K 9/51* (2006.01)
(Continued)

(52) U.S. Cl.
CPC ............ *A61K 9/5138* (2013.01); *A61K 47/10* (2013.01); *C08F 32/02* (2013.01); *C08G 61/08* (2013.01); *C08G 2261/418* (2013.01)

(58) Field of Classification Search
None
See application file for complete search history.

(56) References Cited

U.S. PATENT DOCUMENTS 5,500,223 A  3/1996 Behan et al.
2008/0268035 A1  10/2008 Kim et al.
(Continued)

FOREIGN PATENT DOCUMENTS

WO  2011163637 A2  12/2011
WO  2014064255 A2  5/2014

OTHER PUBLICATIONS

Burt, "Essential Oils: Their antibacterial properties and potential applications in foods—a review";International Journal of Food Microbiology;2004;94:223-253.
(Continued)

Primary Examiner — Brian Gulledge
(74) Attorney, Agent, or Firm — Cantor Colburn LLP

(57) ABSTRACT

A nanocapsule includes a liquid hydrophobic care including an essential oil, and a shell encapsulating the core. The shell includes a copolymer having repeating units of Formula (I) and (II) wherein X, $L^1$, $R^1$, $R^2$, y, and p are as described herein. A dispersion is also disclosed, wherein the dispersion includes a plurality of nanocapsules. The nanocapsules described herein are particularly useful for the treatment of bacterial biofilms.

(Continued)

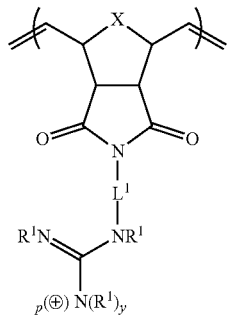

(I)

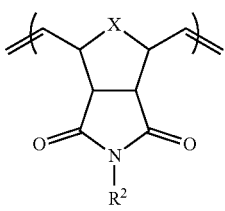

(II)

19 Claims, 16 Drawing Sheets

(51) Int. Cl.
  *A61K 47/10* (2017.01)
  *C08F 32/02* (2006.01)
  *C08G 61/08* (2006.01)

(56) References Cited

U.S. PATENT DOCUMENTS

2013/0280237 A1* 10/2013 Tew .................. A61K 47/32
 424/130.1
2014/0045692 A1* 2/2014 Rossines .............. A61K 9/1075
 504/189

OTHER PUBLICATIONS

Busscher et al.; "Biofilm Formation on Dental Restorative and Implant Materials." J. Dent. Res.;2010;89:657-665.
Carpenter et al.; "Dual Action Antimicrobials: Nitric Oxide Release from Quaternary Ammonium-Functionalized Silica Nanoparticles." Biomacromolecules; 2012;13:3334-3342.
Chang et al.; "Physicochemical Properties and Antimicrobial Efficacy of Carvacrol Nanoemulsions Formed by Spontaneous Emulsification." J. Agric. Food Chem.;2013;61:8906-8913.
Chen et al.; "Impacts of Sample Preparation Methods on Solubility and Antilisterial Characteristics of Essential Oil Components in Milk." Appl. Environ. Microbiol.;2014;80:907-916.
Costerton et al.; "The Application of Biofilm Science to the Study and Control of Chronic Bacterial Infections." J. Clin. Invest;2003;112:1466-1477.
Costerton et al.;"Biofilm in Implant Infections: Its Production and Regulation.";Int. J. Artif. Organs; 2005;28:1062-1068.
Costerton et al; "Bacterial Biofilms: A Common Cause of Persistent Infections."; Science; 1999; 284: 1318-1322.
Ehrlich et al.; "Mucosal Biofilm Formation on Middle-Ear Mucosa in the Chinchilla Model of Otitis Media." JAMA; 2002;287:1710.
Gomes, et al."Poly (DL-lactide-co-glycolide) (PLGA) Nanoparticles with Entrapped trans-Cinnanaldehyde and Eugenol for Antimicrobial Delivery Applications"; Journal of Food Science;2011;76:N16-N24.
Goswami et al.,; "Biocompatible Nanocarrier Fortified with a Dipyridinium-Based Amphiphile for Eradication of Biofilm." ACS Appl. Mater. Interfaces;2014;6:16384-16394.
Hemaiswarya et al.' "Synergism between Natural Products and Antibiotics against Infectious Diseases." Phytomedicine; 2008;15:639-652.
International Search Report; International Application No. PCT/US16/47134; International Filing Date Aug. 16, 2016; dated Nov. 3, 2016; 2 pages.
James et al.; "Biofilms in Chronic Wounds. Wound Repair Regen." 2007;16:37-44.
Kalemba, et al., "Antibacterial and Antifungal Properties of Essential Oils", Curr. Med. Chem. 2003,10,813-829.
Kavanaugh et al.;"Selected Antimicrobial Essential Oils Eradicate *Pseudomonas* Spp. and *Staphylococcus aureus* Biofilms." Appl. Environ. Microbiol.;2012;78:4057-4061.
Levy et al.; "Antibacterial Resistance Worldwide: Causes, Challenges and Responses." Nat. Med.; 2004;10:S122-S129.
Liang et al.' "Physical and Antimicrobial Properties of Peppermint Oil Nanoemulsions." J. Agric. Food Chem.;2012;60:7548-7555.
Lindsay et al, "Bacterial Biofilms within the Clinical Setting: What Healthcare Professionals Should Know." J. Hosp. Infect;2006;64:313-325.
Lynch et al.;"Bacterial and Fungal Biofilm Infections." Annu. Rev. Med.;2008;59:415-428.
Marion-Ferey et al.; "Biofilm Removal from Silicone Tubing: An Assessment of the Efficacy of Dialysis Machine Decontamination Procedures Using an in Vitro Model." J. Hosp. Infect.;2003;53:64-71.
Nostro et al.; "Effects of Oregano, Carvacrol and Thymol on *Staphylococcus aureus* and *Staphylococcus Epidermidis* Biofilms." J. Med. Microbiol.;2007;56:519-523.
Radovic-Moreno et al.;"Surface Charge-Switching Polymeric Nanoparticles for Bacterial Cell Wall-Targeted Delivery of Antibiotics." ACS Nano; 2012;6:4279-4287.
Shalel et al,; "The Mechanism of Hemolysis by Surfactants: Effect of Solution Dispersion." J. Colloid Interface Sci.;2002;252:66-76.
Stewart et al."Antibiotic Resistance of Bacteria in Biofilms." Lancet; 2001;358;135:138.
Szomolay et al. "Adaptive Responses to Antimicrobial Agents in Biofilms." Environ. Microbiol.;2005;7:1186-1191.
Wilhelm et al. "Surfactant-Induced Skin Irritation and Skin Repair." J. Am. Acad. Dermatol.;1994;30:944-949.
Written Opinion of the International Searching Authority; International Application No. PCT/US16/47134; International Filing Date Aug. 16, 2016; dated Nov. 3, 2016; 9 pages.
Zhu et al.; "Nanomedicine in the Management of Microbial Infection—Overview and Perspectives." Nano Today; 2014;9:478-498.

* cited by examiner

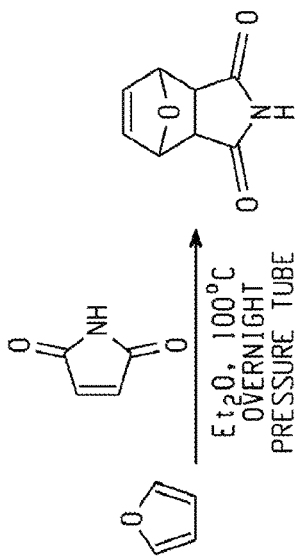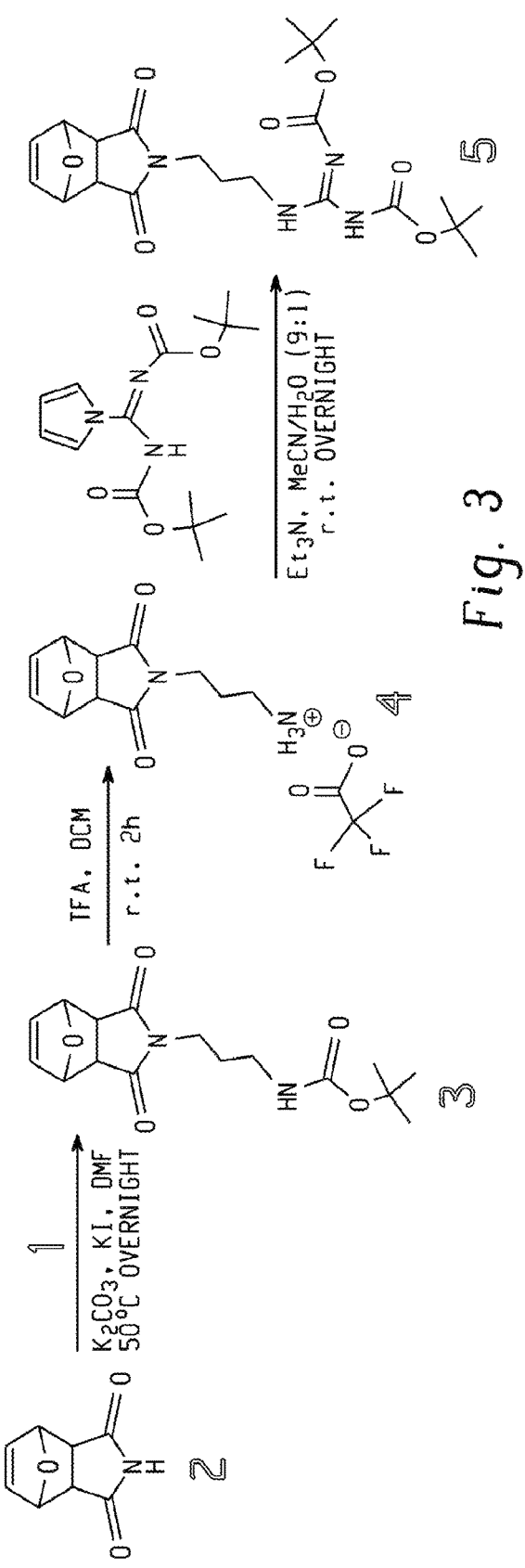
Fig. 1
Fig. 2
Fig. 3

STABILIZED POLYMERIC NANOCAPSULES, DISPERSIONS COMPRISING THE NANOCAPSULES, AND METHODS FOR THE TREATMENT OF BACTERIAL BIOFILMS

CROSS-REFERENCE TO RELATED APPLICATIONS

This application is a National Stage application of PCT/US2016/047134, filed Aug. 16, 2016, which claims the benefit of U.S. Provisional Application No. 62/213,779, filed Sep. 3, 2015, both of which are incorporated by reference herein in their entirety.

BACKGROUND

Bacterial biofilms are highly resilient microbial assemblies that are difficult to eradicate. See, e.g., Costerton, J. W.; Stewart, P. S.; Greenburg, E. P. Bacterial Biofilms: A Common Cause of Persistent Infections. *Science* 1999, 284, 1318-1322. These robust biofilms frequently occur on synthetic implants and indwelling medical devices including urinary catheters, arthro-prostheses, and dental implants. See, e.g., Lindsay, D.; von Holy, A. Bacterial Biofilms within the Clinical Setting: What Healthcare Professionals Should Know. *J. Hosp. Infect.* 2006, 64, 313-325; Costerton, J. W.; Montanaro, L.; Arciola, C. R. Biofilm in Implant Infections: Its Production and Regulation. *Int. J. Artif. Organs* 2005, 28, 1062-1068; Busscher, H. J.; Rinastiti, M.; Siswomihardjo, W.; van der Mei, H. C. Biofilm Formation on Dental Restorative and Implant Materials. *J. Dent. Res.* 2010, 89, 657-665. Biofilm proliferation can also occur on dead or living tissues, leading to endocarditis, otitis media, and chronic wounds. See, e.g., Costerton, W.; Veeh, R.; Shirtliff, M.; Pasmore, M.; Post, C.; Ehrlich, G. The Application of Biofilm Science to the Study and Control of Chronic Bacterial Infections. *J. Clin. Invest.* 2003, 112, 1466-1477; Ehrlich, G.; Veeh, R.; Wang, X.; Costerton, J. W.; Hayes, J. D.; Hu, F. Z.; Daigle, B. J.; Ehrlich, M. D.; Post, J. C. Mucosal Biofilm Formation on Middle-Ear Mucosa in the Chinchilla Model of Otitis Media. *JAMA* 2002, 287, 1710; James, G. A; Swogger, E.; Wolcott, R.; Pulcini, E. deLancey; Secor, P.; Sestrich, J.; Costerton, J. W.; Stewart, P. S. Biofilms in Chronic Wounds. *Wound Repair Regen.* 2007, 16, 37-44. The persistent infections and their concomitant diseases are challenging to treat, as biofilms develop a high resistance to host immune responses and the extracellular polymeric substances limit antibiotic penetration into biofilms. See, e.g., Stewart, P. S.; Costerton, J. W. Antibiotic Resistance of Bacteria in Biofilms. *Lancet* 2001, 358, 135-138; Szomolay, B.; Klapper, I.; Dockery, J.; Stewart, P. S. Adaptive Responses to Antimicrobial Agents in Biofilms. *Environ. Microbiol.* 2005, 7, 1186-1191. Current techniques to remove biofilms on man-made surfaces include disinfecting the surface with bleach or other caustic agents. See, e.g., Marion-Ferey, K.; Pasmore, M.; Stoodley, P.; Wilson, S.; Husson, G. P.; Costerton, J. W. Biofilm Removal from Silicone Tubing: An Assessment of the Efficacy of Dialysis Machine Decontamination Procedures Using an in Vitro Model. *J. Hosp. Infect.* 2003, 53, 64-71. Biofilms in biomedical contexts are very challenging, with therapies based on excising infected tissues combined with long-term antibiotic therapy, incurring high health care costs and low patient compliance due to the invasive treatment. See, e.g., Lynch, A. S.; Robertson, G. T. Bacterial and Fungal Biofilm Infections. *Annu. Rev. Med.* 2008, 59, 415-428. This issue is exacerbated by the exponential rise in antibiotic resistant bacteria. See, e.g., Levy, S. B.; Marshall, B. Antibacterial Resistance Worldwide: Causes, Challenges and Responses. *Nat. Med.* 2004, 10, S122-S129.

Phytochemicals have emerged as a promising alternative to traditional antimicrobials to treat antibiotic resistant bacteria. See, e.g., Kalemba, D.; Kunicka, A. Antibacterial and Antifungal Properties of Essential Oils. *Curr. Med. Chem.* 2003, 10, 813-829; Hemaiswarya, S.; Kruthiventi, A. K.; Doble, M. Synergism between Natural Products and Antibiotics against Infectious Diseases. *Phytomedicine* 2008, 15, 639-652. These essential oils and natural compounds are of particular interest as "green" antimicrobial agents due to their low-cost, biocompatibility, and potential anti-biofilm properties. See, e.g., Burt, S. Essential Oils: Their Antibacterial Properties and Potential Applications in Foods—a Review. *Int. J. Food Microbiol.* 2004, 94, 223-253; Kavanaugh, N. L.; Ribbeck, K. Selected Antimicrobial Essential Oils Eradicate *Pseudomonas* Spp. and *Staphylococcus Aureus* Biofilms. *Appl. Environ. Microbiol.* 2012, 78, 4057-4061; Nostro, A.; Sudano Roccaro, A.; Bisignano, G.; Marino, A.; Cannatelli, M. A; Pizzimenti, F. C.; Cioni, P. L.; Procopio, F.; Blanco, A. R. Effects of Oregano, Carvacrol and Thymol on *Staphylococcus Aureus* and *Staphylococcus Epidermidis* Biofilms. *J. Med. Microbiol.* 2007, 56, 519-523. The generally poor aqueous solubility and stability of these oils has substantially limited their widespread application. See, e.g., Chen, H.; Davidson, P. M.; Zhong, Q. Impacts of Sample Preparation Methods on Solubility and Antilisterial Characteristics of Essential Oil Components in Milk. *Appl. Environ. Microbiol.* 2014, 80, 907-916. Engineering nanomaterials provides a potential platform to prevent payload degradation and to tune molecular interactions with bacteria. See, e.g., Carpenter, A. W.; Worley, B. V; Slomberg, D. L.; Schoenfisch, M. H. Dual Action Antimicrobials: Nitric Oxide Release from Quaternary Ammonium-Functionalized Silica Nanoparticles. *Biomacromolecules* 2012, 13, 3334-3342; Zhu, X.; Radovic-Moreno, A. F.; Wu, J.; Langer, R.; Shi, J. Nanomedicine in the Management of Microbial Infection—Overview and Perspectives. *Nano Today* 2014, 9, 478-498; Radovic-Moreno, A. F.; Lu, T. K.; Puscasu, V. a; Yoon, C. J.; Langer, R.; Farokhzad, 0. C. Surface Charge-Switching Polymeric Nanoparticles for Bacterial Cell Wall-Targeted Delivery of Antibiotics. *ACS Nano* 2012, 6, 4279-4287; Goswami, S.; Thiyagarajan, D.; Das, G.; Ramesh, A. Biocompatible Nanocarrier Fortified with a Dipyridinium-Based Amphiphile for Eradication of Biofilm. *ACS Appl. Mater. Interfaces* 2014, 6, 16384-16394. Previous reports have shown that encapsulating essential oils into surfactant-stabilized colloidal delivery vehicles improves their aqueous stability and increases the antimicrobial activity of small molecule payloads. See, e.g., Chang, Y.; McLandsborough, L.; McClements, D. J. Physicochemical Properties and Antimicrobial Efficacy of Carvacrol Nanoemulsions Formed by Spontaneous Emulsification. *J. Agric. Food Chem.* 2013, 61, 8906-8913; Liang, R.; Xu, S.; Shoemaker, C. F.; Li, Y.; Zhong, F.; Huang, Q. Physical and Antimicrobial Properties of Peppermint Oil Nanoemulsions. *J. Agric. Food Chem.* 2012, 60, 7548-7555; Gomes, C.; Moreira, R. G.; Castell-Perez, E. Poly (DL-Lactide-Co-Glycolide) (PLGA) Nanoparticles with Entrapped Trans-Cinnamaldehyde and Eugenol for Antimicrobial Delivery Applications. *J. Food Sci.* 2011, 76, N16-N24. However, these carriers often induce adverse hemolytic or irritating effects restricting their compatibility with biological tissues. See, e.g., Shalel, S.; Streichman, S.; Marmur, A. The Mechanism of Hemolysis by Surfactants: Effect of Solution Dispersion. *J. Colloid Interface Sci.* 2002, 252, 66-76; Wilhelm, K.-P.; Freitag, G.;

Wolff, H. H. Surfactant-Induced Skin Irritation and Skin Repair. *J. Am. Acad. Dermatol.* 1994, 30, 944-949.

Therefore there remains a need to develop improved carrier systems to achieve effective encapsulation and delivery of essential oils for antimicrobial applications. Polymer-stabilized nanocapsules provide an analogous route to encapsulate hydrophobic materials within a self-assembled polymer shell that is highly resistant to coalescence. Furthermore, polymers embedded at the oil/water interface can also be amenable to post-assembly functionalization to create structurally diverse carriers not achievable when using surfactant stabilized emulsions.

BRIEF SUMMARY

One embodiment is a nanocapsule comprising a liquid hydrophobic core comprising an essential oil; and a shell encapsulating the core, the shell comprising a copolymer comprising repeating units of Formula (I) and (II)

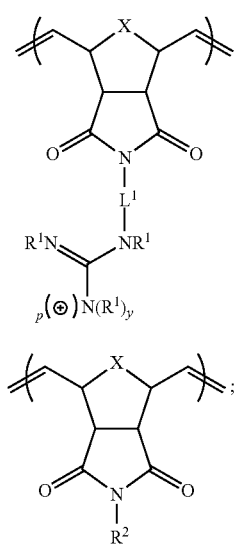

wherein X is independently at each occurrence —O—, —S—, —CH$_2$—, —(CR$^4$R$^5$)—, or

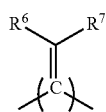

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein is z is an integer from 1 to 10, a divalent a C$_{1-20}$ alkylene oxide group, or a divalent poly(C$_{1-6}$ alkylene oxide) group; R$^1$ is independently at each occurrence hydrogen, a C$_{1-12}$ alkylene group, or a —C(=O)—O—(C$_{1-6}$ alkyl) group; y is 2 or 3; p is 0 or 1; and R$^2$ is independently at each occurrence a C$_{1-12}$ alkylene group, a C$_{6-20}$ arylene group, a C$_{1-20}$ alkylene oxide group, a poly(C$_{1-6}$ alkylene oxide) group, or a zwitterionic group.

Another embodiment is a dispersion comprising a plurality of the above-described nanocapsules.

Another embodiment is a method of treating a bacterial biofilm comprising contacting a dispersion comprising a plurality of the nanocapsules with a bacterial biofilm.

These and other embodiments are described in detail below.

BRIEF DESCRIPTION OF THE DRAWINGS

The following Figures represent exemplary embodiments:

FIG. 1 is a chemical scheme illustrating the synthesis of compound 1.

FIG. 2 is a chemical scheme illustrating the synthesis of compound 2.

FIG. 3 is a chemical scheme illustrating the synthesis of compounds 3, 4, and 5.

DETAILED DESCRIPTION

Figure 4:
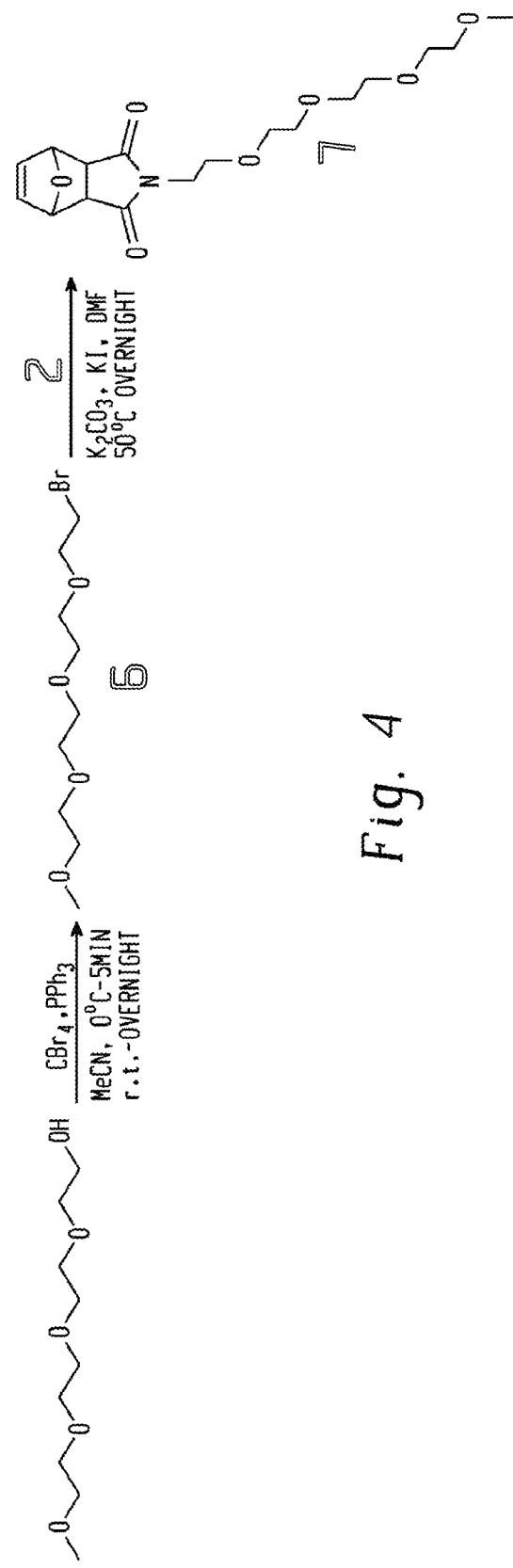
FIG. 4 is a chemical scheme illustrating the synthesis of compounds 6 and 7.

The present inventors have discovered crosslinkable, polymer-stabilized nanocomposites, which can be particularly useful for the treatment of multidrug-resistant biofilms. In particular, the present inventors have successfully prepared polymer nanocapsules comprising an essential oil from guanidine-containing copolymers. The polymers can be prepared by ring-opening metathesis polymerization (ROMP) of suitable monomers. The present inventors have surprisingly found that stable nanocapsules can be prepared from these copolymers, and the nanocapsules can be particularly useful for the treatment of bacterial biofilms, including both in vivo treatments and topical treatments. In an advantageous feature, the nanocapsules can be cross-linked to provide additional stability.

One aspect of the present disclosure is a nanocapsule. The nanocapsules can be core-shell nanocapsules, comprising a core and a shell encapsulating the core.

The nanocapsule shell comprises a copolymer comprising repeating units of Formula (I) and (II)

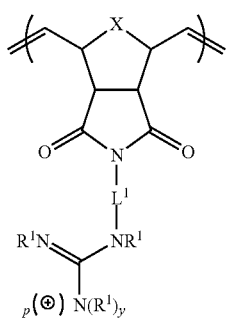

(I)

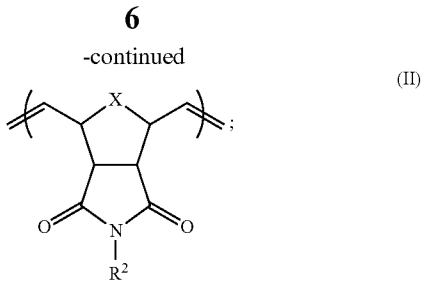

wherein X is independently at each occurrence —O—, —S—, —CH$_2$—, —(CR$^4$R$^5$)—, or

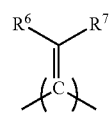

wherein R$^4$ and R$^5$ are independently at each occurrence a C$_{1-6}$ alkyl group and R$^6$ and R$^7$ are independently at each occurrence hydrogen or a C$_{1-6}$ alkyl group. In some embodiments, X is —O—. L$^1$ is independently at each occurrence a divalent group that is (—CH$_2$—)$_z$, wherein z is an integer from 1 to 10 (e.g., 1, 2, 3, 4, 5, 6, 7, 8, 9, or 10), a divalent a C$_{1-20}$ alkylene oxide group, or a divalent poly(C$_{1-6}$ alkylene oxide) group. In some embodiments, L$^1$ is propylene. R$^1$ is independently at each occurrence hydrogen, a C$_{1-12}$ alkylene group, or a —C(=O)—O—(C$_{1-6}$ alkyl) group, y is 2 or 3, and p is 0 or 1. In some embodiments, R$^1$ is hydrogen. In some embodiments, y is 2 and p is 0. In some embodiments y is 3 and p is 1. In some embodiments, when y is 3 and p is 1, the repeating units of Formula (I) can optionally include a counterion, for example chloride, bromide, trifluoroacetate, acetate, citrate, lactate, succinate, propionate, butyrate, ascorbate, maleate, folate, iodide, fluoride, phosphate, sulfonate, carbonate, or a combination thereof. R$^2$ is independently at each occurrence a C$_{1-12}$ alkylene group, a C$_{6-20}$ arylene group, a C$_{1-20}$ alkylene oxide group, a poly (C$_{1-6}$ alkylene oxide) group, or a zwitterionic group. A zwitterionic group is a group of the formula -L$^3$-A-B—C, wherein L$^3$ is a linking group that is (—CH$_2$—)$_q$, wherein q is an integer from 1 to 10 (e.g., 1, 2, 3, 4, 5, 6, 7, 8, 9, or 10), A is a center of permanent positive charge or a center of permanent negative charge, B is a divalent group comprising a C$_{1-12}$ alkylene group, a C$_{6-30}$ arylene group, or an alkylene oxide group, and C is a center of permanent negative charge or a center of permanent positive charge, provided that the zwitterion has an overall net charge of zero (i.e., the zwitterion is net neutral). For example, in an embodiment wherein A is a center of permanent positive charge, C is a center of permanent negative charge. For example, in an embodiment wherein A is a center of permanent negative charge, C is a center of permanent positive charge. In some embodiments, a center of permanent positive charge can include a quaternary ammonium group, a phosphonium group, a sulfonium group, and the like. In some embodiments, the center of permanent positive charge is preferably an ammonium group. In some embodiments, a center of permanent negative charge can include a sulfonate group, a phosphonate group, a carboxylate group, a thiolate group, and the like. In some embodiments, the zwitterionic group is a sulfobetaine group or a carboxy betaine group. In an embodiment, the zwitterionic group is a sulfobetaine group wherein L$^3$ is ethylene, A is ammonium (e.g., a divalent dimethyl ammonium group (—N$^+$(CH$_3$)$_2$—)), B is propylene, and C is a sulfonate group (—SO$_2$O$^-$). In an embodiment, the zwitterionic group is a carboxy betaine group wherein L$^3$ is ethylene, A is ammonium (e.g., a divalent dimethyl ammonium group (—N$^+$(CH$_3$)$_2$—)), B is methylene, and C is a carboxylate group (—COO$^-$). In some embodiments, R$^2$ can be a polyethylene oxide group of the formula —(CH$_2$CH$_2$O)$_s$—R$^9$, wherein s is 10 to 1000, and R$^9$ is hydrogen or a C$_{1-6}$ alkyl group, preferably a methyl group. In some embodiments, R$^2$ is preferably a C$_{1-20}$ alkylene oxide group. For example, R$^2$ can be a group having the structure

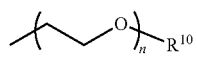

wherein n is 1, 2, 3, or 4, and R$^{10}$ is hydrogen, methyl, or a C$_{1-6}$ alkylamino group (e.g., —(C$_{1-6}$alkyl)-NH$_2$), preferably —CH$_2$CH$_2$NH$_2$). In some embodiments, R$^{10}$ is preferably a methyl group. In some embodiments, n is 4. In a specific embodiment, each occurrence of X is —O—; each occurrence of L$^1$ is propylene; each occurrence of R$^1$ is hydrogen; y is 3; p is 1; and each occurrence of R$^2$ is a group having the structure

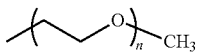

wherein n is 4.

In some embodiments, the molar ratio of units of Formula (I) to units of Formula (II) is 0.5:9 to 9:0.5, for example 1:9 to 9:1, for example 1.5:8.5 to 8.5:1.5, for example 2:8 to 8:2, for example 2.5:7.5 to 7.5:2.5, for example 3:7 to 7:3.

In some embodiments, the copolymer further comprises repeating units of Formula (III)

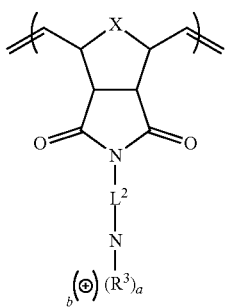

(III)

wherein X is as described above; L$^2$ is independently at each occurrence a divalent group that is (—CH$_2$—)$_z$, wherein z is an integer from 1 to 10 (e.g., 1, 2, 3, 4, 5, 6, 7, 8, 9, or 10), a divalent a C$_{1-20}$ alkylene oxide group, or a divalent poly(C$_{1-6}$ alkylene oxide) group; R$^3$ is independently at each occurrence hydrogen, a C$_{1-12}$ alkylene group, or a —C(=O)—O—(C$_{1-6}$ alkyl) group; a is 2 or 3; and b is 0 or 1. In some embodiments, L$^2$ is propylene. In some embodiments, a is 3 and b is 1. In some embodiments, a is 2 and b is 0.

In an embodiment, the nanocapsule shell comprises a copolymer comprising repeating units of Formula (I), (II), and (III), wherein X, L$^1$, L$^2$, R$^1$, R$^2$, R$^3$, y, p, a, and b can be as described above. In an embodiment, each occurrence of X is —O—; each occurrence of L$^1$ and L$^2$ are propylene; each occurrence of R$^1$ is hydrogen; each occurrence of y is 3; each occurrence of p is 1; each occurrence of R$^2$ is a group having the structure

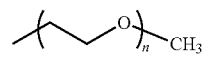

wherein n is 4; each occurrence of R$^3$ is hydrogen; each occurrence of a is 3; and each occurrence of b is 1.

In some embodiments, the copolymer comprises 5 to 50 mole percent, or 25 to 45 mole percent, or 30 to 40 mole percent of repeating units of Formula (I); 10 to 50 mole percent, or 20 to 40 mole percent, or 25 to 35 mole percent of repeating units of Formula (II); and 0 to 50 mole percent, or 25 to 45, or 30 to 40 mole percent of repeating units of Formula (III), wherein the mole percent of each component is based on the total moles of the copolymer. In a specific embodiment, the copolymer comprises 30 to 40 mole percent, preferably 35 mole percent repeating units of Formula (I), 25 to 35 mole percent, preferably 30 mole percent repeating units of Formula (II), and 30 to 40 mole percent, preferably 35 mole percent repeating units of Formula (III).

The copolymer can be a block copolymer or a random copolymer. In some embodiments, the copolymer is a random copolymer. In some embodiments, the copolymer has a number average molecular weight, as determined by gel permeation chromatography, of 1,000 to 100,000 Daltons (Da), for example 3,000 to 100,000 Da, for example 10,000 to 100,000 Da, for example 10,000 to 75,000 Da, for example 10,000 to 50,000 Da, for example 10,000 to 30,000 Da.

The copolymer can be prepared by any method which is generally known. For example, the copolymer can be prepared by ring opening metathesis polymerization (ROMP) of a suitable cyclic olefin monomer (e.g., norbornene, oxanorbornene, derivatives thereof, and the like) in the presence of a ROMP catalyst such as a ruthenium-containing catalyst. An example of such a procedure is described in the working examples below.

In some embodiments, the copolymer can optionally further comprise repeating units comprising a degradable linker (also referred to as "degradable repeating units"). The degradable linker can be hydrolytically degradable, enzymatically degradable, or a combination thereof. In some embodiments, the degradable linker comprises an ester group (—C(=O)—O—). Exemplary repeating units comprising a degradable linker can include those of the formula (IV)

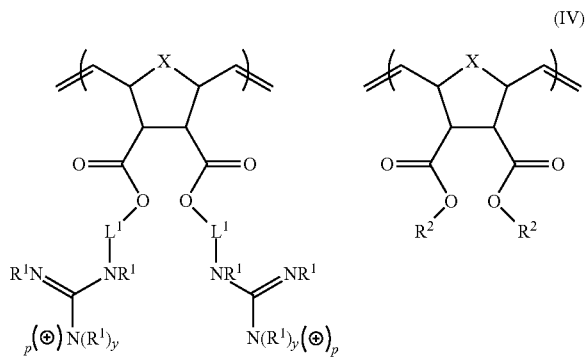

(IV)

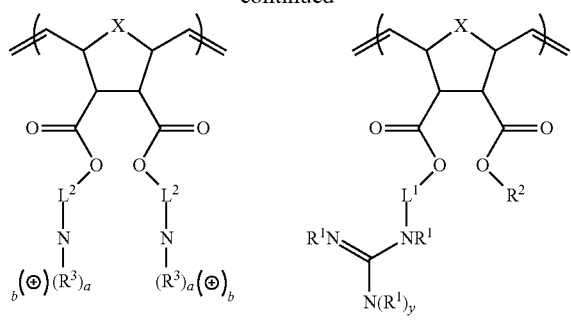

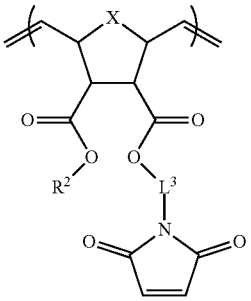

wherein X and $R^2$ can be as described above, and $R^2$ is preferably a $C_{1-12}$ alkylene group, more preferably a $C_{1-6}$ alkylene group, and $L^3$ is a divalent group that is $(-CH_2-)_z$, wherein z is an integer from 1 to 10 (e.g., 1, 2, 3, 4, 5, 6, 7, 8, 9, or 10). For example, in some embodiments, the crosslinkable repeating unit can be of formula (VA)

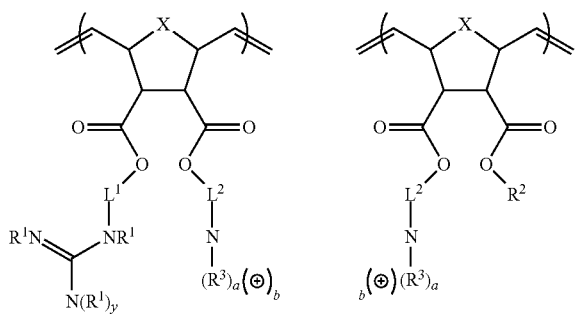

wherein each occurrence of X, $L^1$, $R^1$, y, p, $R^2$, $L^2$, $R^3$, a, and b are as defined above. In some embodiments, each occurrence of X is —O—; each occurrence of $L^1$ and $L^2$ are propylene; each occurrence of $R^1$ is hydrogen; each occurrence of y is 3; each occurrence of p is 1; each occurrence of $R^2$ is a group having the structure

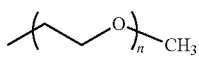

wherein n is 4; each occurrence of $R^3$ is hydrogen; each occurrence of a is 3; and each occurrence of b is 1. When present, the degradable repeating units can be included in the copolymer in an amount of 5 to 95 mole percent, based on the total moles of the copolymer. Within this range, the degradable repeating units can be present in an amount of at least 10, 15, 20, 25, 30, 35, 40, 45, 50, 60, 70, 75, or 80 mole percent. Also within this range, the degradable repeating units can be present in an amount of less than or equal to 90, 85, 80, 75, 70, 65, 60, 55, 50, 45, 40, 35, 30, 25 or 20 mole percent.

In some embodiments, the copolymer can optionally further comprise crosslinkable repeating units, which, in some embodiments, can facilitate degradation (e.g., biodegradation) of the polymer nanocapsules prepared therefrom. In some embodiments, the crosslinkable repeating units comprise a maleimide group. Exemplary crosslinkable repeating units can include, for example, repeating units of the formula (V)

A crosslinkable repeating unit comprising a maleimide group can be crosslinked, for example, through addition of a dithiol-disulfide crosslinker. The thiol moieties of the dithiol-disulfide can react with the maleimide groups to form stable thioether bonds, while the disulfide group can be degradable, for example, under reducing conditions. Additional functionality, for example ester linkages, can also be included in the dithiol-disulfide crosslinker to facilitate further degradation, for example through hydrolysis. An example of the preparation of such crosslinked, degradable nanocapsules is further described in the working examples below.

When present, the crosslinkable repeating units can be included in the copolymer in an amount of 5 to 95 mole percent, based on the total moles of the copolymer. Within this range, the crosslinkable repeating units can be present in an amount of at least 10, 15, 20, 25, 30, 35, 40, 45, 50, 60, 70, 75, or 80 mole percent. Also within this range, the crosslinkable repeating units can be present in an amount of less than or equal to 90, 85, 80, 75, 70, 65, 60, 55, 50, 45, 40, 35, 30, 25 or 20 mole percent In some embodiments, the exterior of the shell of the nanocapsule comprises one or more amine groups, for example due to the presence of repeating units of Formula (III). In some embodiments, the exterior of the shell of the nanocapsule can optionally be further functionalized with any moiety containing an amine-reactive group. In some embodiments, the surface of the nanocapsule can be further functionalized so as to provide a desired effect, including a therapeutic effect, a targeting effect, or an imaging effect. In some embodiments, functionalization of the shell of the nanocapsule can increase the interaction of the nanocapsule with a bacterial biofilm. In some embodiments, functionalization can include reacting an organic molecule with an amine on the surface of the nanocapsule, wherein the organic molecule can include a carboxylic acid capable of reacting with an amine (e.g., to form an amide, —C(=O)—NH—). Exemplary organic molecules can include, for example, 4-carboxyphenyl boronic acid, aldonic acid, ulosonic acid, uronic acid, and the like, and combinations thereof. In some embodiments, functionalization can include reacting a fluorescent, luminescent or phosphorescent compound with an amine on the surface of the nanocapsule, for example reacting fluorescein isothiocyanate or a derivative thereof or tetramethylrhodamine isothiocyanate or a derivative thereof to provide a fluorescein- or rhodamine-labelled nanocapsule.

In addition to the shell, the nanocapsule comprises a liquid hydrophobic core comprising an essential oil. The liquid hydrophobic core is generally a liquid at 25° C. The essential oil can be a naturally occurring compound (e.g., derived from a plant). Essential oils, as used herein, are volatile aromatic oils which can be synthetic or derived from plants (e.g., flowers, buds, seeds, leaves, twigs, bark, herbs, wood, fruits, roots, and the like) by a physical method (e.g., distillation, expression, fermentation, or extraction). Essential oils usually carry the odor or flavor of the plant from which they are obtained. The essential oil is preferably an oil having antimicrobial properties. In some embodiments, the essential oil can be selected from, for example, peppermint oil, oregano oil, thymol, menthol, methyl salicylate, eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, or a combination thereof. In some embodiments, the essential oil is selected from carvacrol oil, limonene, peppermint oil, cilantro oil, coriander oil, cinnamon oil, oregano oil, rosemary oil, sage oil, clove oil, thyme oil, or a combination thereof. In some embodiments, the essential oil comprises carvacrol oil, limonene, or a combination thereof. In some embodiments, the essential oil comprises carvacrol oil.

In some embodiments, the core further comprises a hydrophobic anhydride-containing polymer. The hydrophobic anhydride-containing polymer is preferably soluble in the essential oil. In some embodiments, the anhydride-containing polymer comprises at least two types of repeating units (i.e., the anhydride-containing polymer is a copolymer), preferably a repeating unit comprising an anhydride group (e.g., maleic anhydride), and a repeating unit comprising a hydrophobic group. The anhydride-containing polymer includes more than one anhydride group, which can be incorporated into the backbone of the polymer, included as a pendent group, or a combination thereof. The hydrophobic anhydride-containing polymer can be a random copolymer, a graft copolymer, or an alternating copolymer, preferably an alternating copolymer. In some embodiments, the anhydride-containing polymer preferably comprises repeating units derived from maleic anhydride. For example, in some embodiments, the hydrophobic anhydride-containing polymer is an alternating copolymer comprising repeating units of Formula (VI)

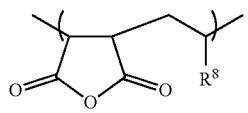

wherein $R^8$ is independently at each occurrence a hydrogen, a $C_{1-20}$ alkyl group, a $C_{6-20}$ aryl group, or a —O—($C_{1-12}$ alkyl) group. In some embodiments, $R^8$ can be a phenyl group, a hydrogen, a methyl group, an ethyl group, a propyl group, a butyl group, a hexyl group, an octyl group, a decyl group, a dodecyl group, a hexadecyl group, and the like, or a combination thereof, preferably a hexadecyl group. The anhydride-containing polymer can be prepared by any method that is generally known, for example by copolymerization of maleic anhydride and at least one of styrene, isoprene, ethylene, propylene, methyl vinyl ether, octadecene, and the like, or a combination thereof. The anhydride-containing polymer can have a number average molecular weight of 3,000 to 100,000 Daltons (Da), or 10,000 to 100,000 Da, or 15,000 to 80,000 Da, or 20,000 to 60,000 Da, or 30,000 to 50,000 Da.

When present, the hydrophobic anhydride-containing polymer can be included in the core in an amount of 0.01 to 15 weight percent, or 0.5 to 12 weight percent, or 1 to 10 weight percent, based on the total weight of the core.

In some embodiments, at least a portion of the shell is crosslinked with the anhydride-containing polymer. Preferably, at least a portion of the shell is crosslinked with the anhydride-containing polymer when the shell comprises a copolymer comprising repeating units according to Formula (III). As demonstrated in the working examples below, the amine groups of the copolymer (for example, the amine group of each repeating unit of Formula (III)) can react with the anhydride group to form a covalent bond (e.g., a crosslink) comprising the corresponding ring-opened amide and carboxylic acid or carboxylate. In some embodiments, the portion of the shell that is crosslinked with the anhydride-containing polymer refers to the interior of the shell, or the portion of the shell in contact with the core containing the anhydride-containing polymer. In some embodiments, at least 50%, or at least 60%, or at least 70%, or at least 80%, or at least 85% of the amines of the nanocapsule shell have reacted with the anhydride-containing polymer to form a crosslinked nanocapsule shell.

In some embodiments, the core of the nanocapsule can optionally further include a hydrophobic antibiotic. The hydrophobic antibiotic is soluble in the essential oil. The presence of the hydrophobic antibiotic can increase the antimicrobial activity of the nanocapsule. Suitable hydrophobic antibiotics include nalidixic acid, cinoxacin, norfloxacin, ciprofloxacin, enoxacin, ofloxacin, levofloxacin, sparfloxacin, moxifloxacin, gemifloxacin, trovafloxacin, ampicillin, amoxicillin, carbenicillin, carfecillin, ticarcillin, azlocillin, mezlocillin, piperacillin, cefepime, tetracycline, gentamicin, tobramycin, streptomycin, neomycin, kanamycin, amikacin, cefoselis, and cefquinome. When present, the hydrophobic antibiotic can be included in the nanocapsule in an amount of 1 to 10 weight percent, based on the weight of the core.

In some embodiments, the nanocapsules have an average diameter of less than or equal to 500 nanometers (nm), for example 1 to 500 nm, or 10 to 500 nm, or 1 to 250 nm, or 10 to 250 nm, or 1 to 100 nm, or 5 to 100 nm, or 10 to 100 nm, or 15 to 100 nm, or 15 to 90 nm, or 15 to 85 nm, or 20 to 80 nm, or 20 to 75 nm. The average diameter of the capsule can be determined, for example, using light scattering techniques.

In some embodiments, the nanocapsule comprises 90 to 99.9 weight percent, or 90 to 99 weight percent, or 95 to 99 weight percent of the core and 0.1 to 10 weight percent, or 1 to 10 weight percent, or 1 to 5 weight percent of the shell, wherein weight percent is based on the total weight of the nanocapsule.

In an embodiment, the nanocapsule comprises, based on the weight of the nanocapsule, 1 to 10 weight percent of the core and 90 to 99 weight percent of the shell. The core can comprise carvacrol oil, and the shell comprises the copolymer having repeating units of Formula (I) and (II) wherein each occurrence of X is —O—; each occurrence of $L^1$ is propylene; each occurrence of $R^1$ is hydrogen; each occurrence of y is 3; each occurrence of p is 1; each occurrence of $R^2$ is a group having the structure

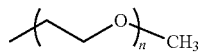

wherein n is 4; and the nanocapsule has a diameter of 1 to 100 nanometers.

In another embodiment, the nanocapsule comprises, based on the weight of the nanocapsule, 1 to 10 weight percent of the core and 90 to 99 weight percent of the shell. The core can comprise carvacrol oil, and the shell comprises repeating units of Formula (I), (II), and (III), wherein each occurrence of X is —O—; each occurrence of $L^1$ and $L^2$ are propylene; each occurrence of $R^1$ is hydrogen; each occurrence of y is 3; each occurrence of p is 1; each occurrence of $R^2$ is a group having the structure

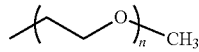

wherein n is 4; each occurrence of $R^3$ is hydrogen; each occurrence of a is 3; each occurrence of b is 1; and the nanocapsule has a diameter of 1 to 100 nanometers.

In another embodiment, the nanocapsule comprises, based on the weight of the nanocapsule, 1 to 10 weight percent of the core and 90 to 99 weight percent of the shell. The core can comprise, based on the weight of the core, 85 to 99.99 weight percent carvacrol oil and 0.01 to 15 weight percent of the hydrophobic anhydride containing polymer comprising repeating units of Formula (VII)

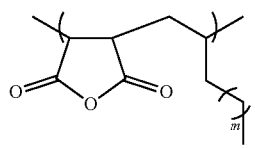

wherein m is an integer from 1 to 16 (e.g., 1, 2, 3, 4, 5, 6, 7, 8, 9, 10, 11, 12, 13, 14, 15, or 16), preferably 10 to 16. The shell comprises repeating units of Formula (I), (II), and (III) wherein each occurrence of X is —O—; each occurrence of $L^1$ and $L^2$ are propylene; each occurrence of $R^1$ is hydrogen; each occurrence of y is 3; each occurrence of p is 1; each occurrence of $R^2$ is a group having the structure

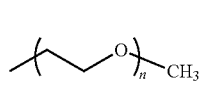

wherein n is 4; each occurrence of $R^3$ is hydrogen; each occurrence of a is 3; each occurrence of b is 1; the nanocapsule has a diameter of 1 to 100 nanometers; and at least a portion of the shell is crosslinked with the anhydride-containing polymer.

Another aspect of the present disclosure is a dispersion comprising a plurality of nanocapsules. As used herein, "plurality of nanocapsules" refers to a dispersion comprising more than 1 nanocapsule, for example more than 10 nanocapsules. In some embodiments, the dispersion comprises 0.01 to 90 weight percent of the nanocapsules. The nanocapsules can include nanocapsules having the above-described structure and components. In some embodiments, the dispersion can be in the form of a gel, a cream, or a paste (e.g., a toothpaste, a topical ointment, and the like). In some embodiments, the dispersion comprises 50 to 90 weight percent, or 50 to 80 weight percent of the nanocapsules, based on the total weight of the dispersion. In some embodiments, the nanocapsules are dispersed in a liquid carrier, for example an aqueous solution or a $C_{1-6}$ alcohol (e.g., ethanol), preferably an aqueous solution. In such an embodiment, the dispersion is in the form of a liquid. In some embodiments, the dispersion comprises 0.01 to 50 weight percent of the nanocapsules, based on the total weight of the dispersion. The aqueous solution can comprise water, deionized water, a buffer (e.g., phosphate buffered saline, phosphate buffer, and the like), and the like, or a combination thereof. The dispersion can optionally further comprise various additives that are generally known in the art, with the proviso that the additives do not significantly adversely affect one or more desired properties of the dispersion. Furthermore, it can be particularly desirable that the presence of an additive does not significantly interfere with the structure of the nanocapsules. Additives can include stabilizers, thickeners, viscosity enhancers, coloring agent, surfactants, emulsifiers, humectants, and the like, or a combination thereof.

When the dispersion comprises the nanocapsules dispersed in an aqueous solution, the nanocapsules can have a surface charge dependent on the pH of the aqueous solution. For example, in some embodiments, the nanocapsules can be positively charged when the pH of the aqueous solution is less than the isoelectric point of the shell copolymer. In some embodiments, when the hydrophobic anhydride-containing polymer is present in the core and at least a portion of the shell is crosslinked, the nanocapsules can be negatively charged. Without wishing to be bound by theory, the negative charge in this embodiment is believed to be associated with the presence of the carboxylate groups formed as a result of the crosslinking reaction between the anhydride-containing polymer and the amines of the shell copolymer.

The dispersions can be prepared by any method that is generally known. For example, an aqueous dispersion comprising the polymer nanocapsules can be prepared by contacting an aqueous solution comprising the copolymer with the hydrophobic liquid (e.g., the essential oil) optionally comprising the anhydride-containing copolymer. The hydrophobic liquid is insoluble in the aqueous solution. Subsequent to contacting the aqueous solution and the hydrophobic liquid, the mixture is emulsified, for example using an amalgamator, or any suitable mixing device. Emulsifying the mixture provides nanocapsules comprising the hydrophobic liquid dispersed in the aqueous solution, wherein the nanocapsules are stabilized by a shell comprising the copolymer. An example of a method for preparing a dispersion according to the present disclosure is provided in the working examples below.

Another aspect of the present disclosure is a method for treating a bacterial biofilm. The method comprises contacting the above-described dispersion with a bacterial biofilm. In some embodiments, the dispersion comprising the nanocapsules can be used as an injectable antimicrobial formulation, and can treat a bacterial biofilm in vivo. In some embodiments, the dispersion comprising the nanocapsules can be used as an antimicrobial ointment for topical treatment of a bacterial biofilm.

A "biofilm" refers to a population of bacteria attached to an inert or living surface. Thus, biofilms can form on a counter, a table, water pipes, implants, catheters, cardiac pacemakers, prosthetic joints, cerebrospinal fluid shunts, endotracheal tubes, and the like. In some embodiments, the biofilm can be present on a living surface, for example skin or in a wound, and on teeth (e.g., dental plaque). Bacteria in a biofilm are enmeshed in an extracellular polymer matrix, generally a polysaccharide matrix, which holds the bacteria together in a mass, and firmly attaches the bacterial mass to the underlying surface. Evidence has shown that biofilms constitute a significant threat to human health. Wounds and skin lesions are especially susceptible to bacterial infection.

In some embodiments, the bacterial biofilm can be a gram-negative bacterial biofilm or a gram-positive bacterial biofilm. In some embodiments, the bacterial biofilm comprises *Escherichia coli* (e.g., *E. coli* DH5α), *Pseudomonas* bacteria (e.g., *Pseudomonas aeruginosa*), *Staphylococcal* bacteria (e.g., *Staphylococcal aureus*), Enterobacteriaceae bacteria (e.g., *E. cloacae* complex), *Streptococcus* bacteria, *Haemophilus influenzae, Leptospira interrogans, Legionella* bacteria, or a combination thereof.

Contacting the dispersion comprising the nanocapsules with a biofilm can effectively kill bacterial cells present in the biofilm. Accordingly, the dispersions disclosed herein can be particularly useful as disinfectants or antimicrobial dispersions. The contacting can be under conditions effective to treat the biofilm, for example for a time of 10 minutes to 5 hours, or 1 hour to 3 hours, and at a temperature of 25 to 37° C. As used herein, "treating a biofilm" can refer to killing at least 20%, or at least 40%, or at leat 50%, or at least 60%, or at least 80%, or at least 90% of the bacterial cells present in the biofilm. In some embodiments, contacting the dispersion with a biofilm can completely remove the biofilm (i.e., the dispersion is toxic to greater than 90%, or 99% or 99.9% of the bacterial cells of the biofilm upon contacting the dispersion with the biofilm).

In summary, the present disclosure provides stabilized polymeric nanocapsules comprising an essential oil-containing core. The stabilized nanocapsules demonstrate highly effective therapeutic behavior, successfully eradicating pathogenic biofilm strains of clinical isolates. These capsules have potential applications as a general surface disinfectant as well as an antiseptic for wound treatment. The self-assembly strategy used to prepare the nanocapsules provides a promising platform to create effective delivery vehicles to combat bacterial biofilms.

The nanocapsules, dispersions, and methods are further illustrated by the following non-limiting examples.

EXAMPLES

Experimental details for the preparation of the copolymers and the nanocapsules are provided below.

Monomer Synthesis

Compound 1, shown in FIG. 1, was synthesized according to the following procedure. To a 500 milliliter round bottom flask equipped with a stir bar, 150 milliliters of dichloromethane (DCM) was added. 3-Bromopropylamine hydrobromide (10.0 grams, 45.7 millimoles, 1.0 molar equivalent) was added to the DCM solution. Triethylamine ($Et_3N$) (25.5 milliliters, 182.7 millimoles, 4.0 molar equivalents) was added to the reaction mixture. Di-tert-butyl dicarbonate (12.6 milliliters, 54.8 millimoles, 1.2 molar equivalents) was then added dropwise to the stirring mixture. After addition of di-tert-butyl dicarbonate was complete, the reaction was stirred overnight at room temperature (r.t.). The DCM was removed by rotary evaporation, diluted with 100 milliliters of diethyl ether, and extracted with 1 molar (M) aqueous hydrochloric acid (HCl) (1×20 milliliters), a saturated aqueous solution of sodium bicarbonate (2×20 milliliters), and brine solution (1×20 milliliters). The organic layer was then dried with sodium sulfate, filtered, and concentrated under reduced pressure to yield compound 1 as a clear liquid. Compound 1 was purified using column chromatography over silica gel as the stationary phase. Proton nuclear magnetic resonance spectroscopy ($^1H$ NMR) was used to confirm the structure of compound 1. $^1H$ NMR was conducted at 400 MHz using deuterated chloroform ($CDCl_3$) as the solvent. The chemical shifts are reported as parts per million (ppm) using tetramethylsilane (TMS) as a reference: 4.6 (br, 1H) 3.43 (t, 2H), 3.26 (br, 2H), 2.04 (t, 2H), 1.43 (s, 9H).

Compound 2, shown in FIG. 2, was synthesized according to the following procedure. In a pressure tube, furan (4.5 milliliters, 61.7 millimoles, 1.5 molar equivalents) and maleimide (4.0 grams, 41.1 millimoles, 1.0 molar equivalent) were added in addition to 5 milliliters of diethyl ether. The tube was sealed and heated at 100° C. overnight. The pressure tube was subsequently cooled to r.t. and the precipitated solid was removed, filtered, and washed with copious amounts of diethyl ether to isolate compound 2 as a white solid, which was used without further purification. $^1H$ NMR (400 MHz, MeOD) 11.14 (s, 1H), 6.52 (s, 2H), 5.12 (s, 2H), 2.85 (s, 2H).

Compound 3, shown in FIG. 3, was synthesized according to the following procedure. To a 100 milliliter round bottom flask equipped with a stir bar, 30 milliliters of dimethylformamide (DMF) was added. Compound 2 (2.36 grams, 14.3 millimoles, 1.0 molar equivalent) was then added with potassium carbonate (7.9 grams, 57.2 millimoles, 4.0 molar equivalents). The reaction mixture was heated at 50° C. for five minutes. Potassium iodide (0.05 grams, 0.30 millimoles, 0.02 molar equivalents) and compound 1 (3.47 grams, 14.6 millimoles, 1.02 molar equivalents) were added and stirred at 50° C. overnight. The reaction mixture was cooled to room temperature, diluted to 150 milliliters with ethyl acetate and washed with water (7×50 milliliters) and brine (1×50 milliliters). The organic layer was dried with sodium sulfate, filtered, and concentrated by rotary evaporation to yield compound 3 as a white solid. Compound 3 was purified using column chromatography and silica gel as the stationary phase. $^1H$ NMR (400 MHz, $CDCL_3$) 6.51 (s, 2H), 5.26 (s, 2H), 5.03 (br, 1H), 3.56 (t, 2H), 3.05 (q, 2H), 2.86 (s, 2H), 1.73 (quint, 2H) 1.45 (s, 9H).

Compound 4, shown in FIG. 3, was synthesized according to the following procedure. To a 50 milliliter round bottom flask equipped with a stir bar was added compound 3 (2.0 grams, 6.2 millimoles, 1.0 molar equivalent). Nitrogen (gas) was bubbled through DCM for five minutes and 5 milliliters was added to the flask which was further purged with nitrogen. 5 milliliters of trifluoroacetic acid (TFA, excess) was added and the reaction mixture was stirred for two hours. Excess TFA was then removed by rotary evaporation with DCM (3×) yielding compound 4. Compound 4 was isolated as a white solid by washing with diethyl ether (3×10 milliliters) and used without further purification and directly used in the next reaction. A ninhydrin test was used to confirm the presence of free primary amine.

Compound 5, shown in FIG. 3, was synthesized according to the following procedure. To a 100 milliliter round bottom flask equipped with a stir bar was added compound 4 (1.2 grams, 3.6 millimoles, 1.0 molar equivalents), 45 milliliters acetonitrile (MeCN), and 5 milliliters of water. Triethylamine (4.7 milliliters, 33.5 millimoles, 9.2 molar equivalents) was added and finally N,N'-Di-Boc-1H-pyrazole-1-carboxamidine (1.7 grams, 5.5 millimoles, 1.5 molar equivalents) in portions. The reaction was allowed to stir at r.t. overnight. The solution was diluted with 100 milliliters of ethyl acetate and extracted with water (2×50 milliliters) and brine (2×50 milliliters). The organic layer was dried with sodium sulfate, filtered, and concentrated by rotary evaporation to yield compound 5. Compound 5 was purified using column chromatography and silica gel as the stationary phase to yield a white solid. $^1$H NMR (400 MHz, CDCl$_3$) 8.49 (t, 1H), 6.49 (s, 2H), 5.25 (s, 2H), 3.53 (t, 2H), 3.47 (q, 2H), 2.83 (s, 2H), 1.82 (quint, 2H), 1.49 (s, 18H).

Compound 6, shown in FIG. 4, was synthesized according to the following procedure. To a 250 milliliter round bottom flask was added tetraethylene glycol monomethyl ether (4.2 milliliters, 20.9 millimoles, 1.0 molar equivalent) and 80 milliliters of MeCN. The reaction was cooled to 0° C. and tetrabromomethane (8.4 grams, 25.1 millimoles, 1.2 molar equivalents) was added. Triphenylphosphine (6.6 grams, 25.3 millimoles, 1.2 molar equivalents) was added in portions and allowed to stir for five minutes at 0° C. After five minutes, the reaction was warmed to room temperature and stirred overnight. The reaction was subsequently concentrated by rotary evaporation and purified using column chromatography and silica gel as the stationary phase to yield compound 6 as a clear oil. $^1$H NMR (400 MHz, CDCl$_3$) 3.75 (t, 2H), 3.6 (br, 10H), 3.49 (t, 2H), 3.41 (t, 2H), 3.32 (s, 3H).

Compound 7, shown in FIG. 4, was synthesized according to the following procedure. To a 100 milliliter round bottom flask equipped with a stir bar was added 30 milliliter of DMF. Compound 2 (2.84 grams, 17.2 millimoles, 1.0 molar equivalents) was added along with potassium carbonate (9.48 grams, 68.7 millimoles, 4.0 molar equivalents). The reaction mixture was heated at 50° C. for five minutes. Potassium iodide (0.05 grams, 0.30 millimoles, 0.02 molar equivalents) and compound 6 (4.9 grams, 18.0 millimoles, 1.05 molar equivalents) were added and stirred at 50° C. overnight. The reaction mixture was then cooled to room temperature, diluted to 150 milliliters with ethyl acetate and washed with water (7×50 milliliters) and brine (1×50 milliliters). The organic layer was dried with sodium sulfate, filtered, and concentrated under reduced pressure to yield compound 7. Compound 7 was isolated as a clear oil using column chromatography and silica gel as the stationary phase, and characterized by $^1$H NMR spectroscopy. $^1$H NMR (400 MHz, CDCl$_3$) 6.49 (s, 2H), 5.23 (s, 2H), 3.66 (t, 2H), 3.6 (br, 8H), 3.58 (br, 4H), 3.51 (t, 2H), 3.35 (s, 3H), 2.83 (s, 2H).

Polymer Synthesis

Figure 5:
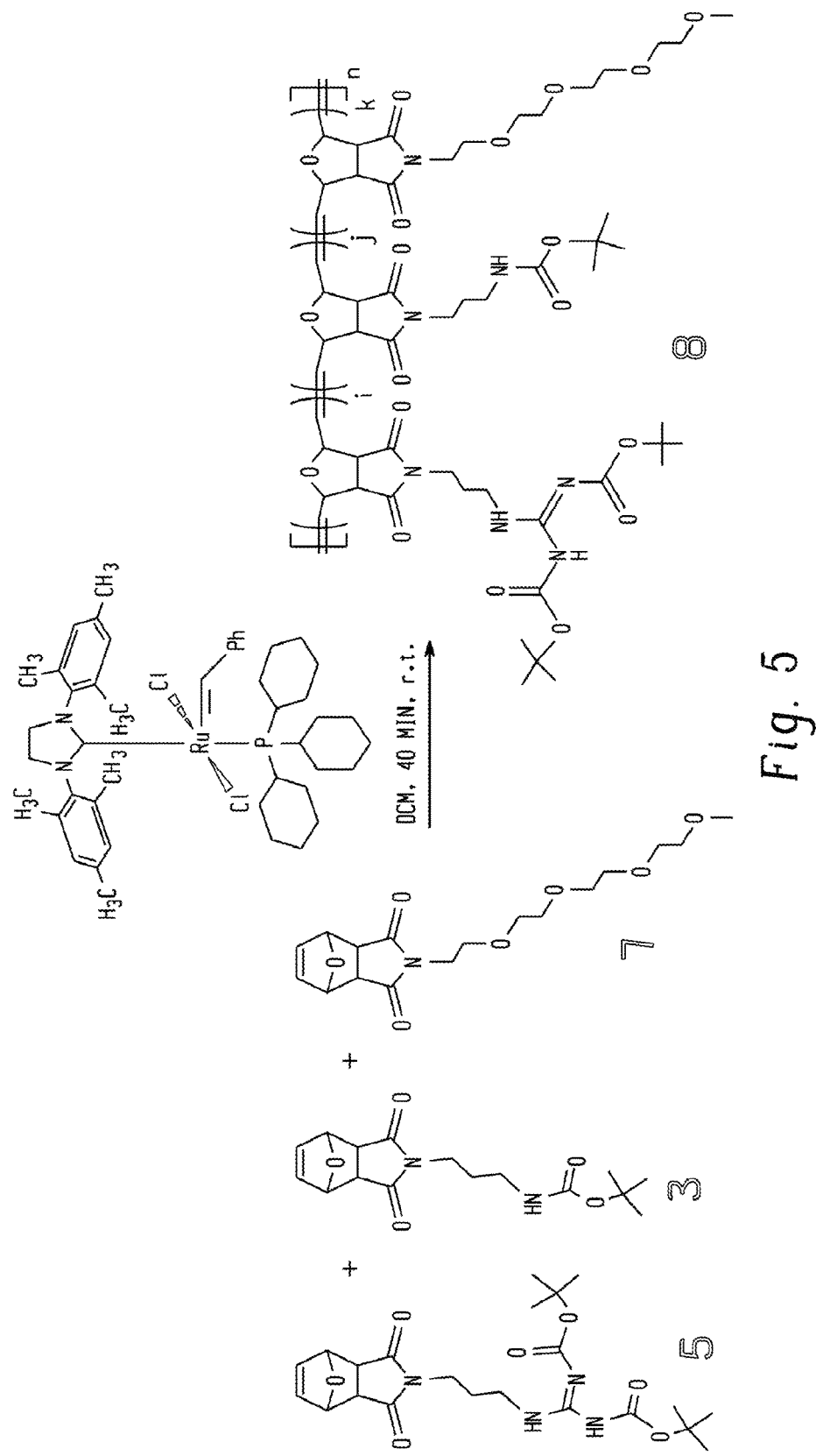
FIG. 5 is a chemical scheme illustrating the synthesis of polymer 8.

Polymer 8, shown in FIG. 5, was synthesized according to the following procedure. To a 10 milliliter pear-shaped flask equipped with a stir bar, compound 5 (457 milligrams, 0.98 millimoles, 1.0 molar equivalent), compound 3 (317 milligrams, 0.98 millimoles, 1.0 molar equivalent) and compound 7 (300 milligrams, 0.84 millimoles, 0.85 molar equivalents) were added. DCM was purged with nitrogen for five minutes and 5 milliliters was then added to the flask. The reaction mixture was properly sealed with a septum and purged with nitrogen for two minutes. The main nitrogen line was left in the septum and the nitrogen pressure was reduced to a steady stream. (1,3-Bis(2,4,6-trimethylphenyl)-2-imidazolidinylidene)dichloro(phenylmethylene)(tricyclohexylphosphine) ruthenium (also known as Grubbs Catalyst 2$^{nd}$ Generation) (83 milligrams, 0.098 millimoles, 0.1 molar equivalent) was dissolved in 1 milliliter of nitrogen-purged DCM and added quickly to the stirring reaction mixture. The flask was shielded from light by covering with aluminum foil. After 40 minutes, ethyl vinyl ether (200 microliters (µl), excess) was quickly added and stirring continued for 15 minutes. The resulting polymer was precipitated into 200 milliliters of 1:1 hexane:ethyl ether. The polymer was collected by filtration, dissolved in a minimal amount of DCM and precipitated again in the same hexane:ethyl ether solution yielding polymer 8 as a purplish-gray solid. The polymer molecular weight was characterized by gel permeation chromatography (GPC) against polystyrene standards eluting with tetrahydrofuran. Polymer 8 was found to have a weight average molecular weight (Mw) of 31,736 Daltons (Da). The polymer was also characterized using $^1$H NMR spectroscopy. $^1$H NMR (400 MHz, CDCl$_3$) 11.4 (s, 1H), 8.39 (br, 1H), 6.01 (s, 2H), 5.72 (br, 2H), 4.95 (br, 2H), 4.41 (br, 2H), 3.55 (br, 11H), 3.32 (br, 2H), 3.30 (s, 2H), 3.29 (br, 2H), 3.01 (br, 1H), 1.82 (br, 1H), 1.7 (br, 3H), 1.42 (s, 12H), 1.35 (s, 6H).

Figure 6:
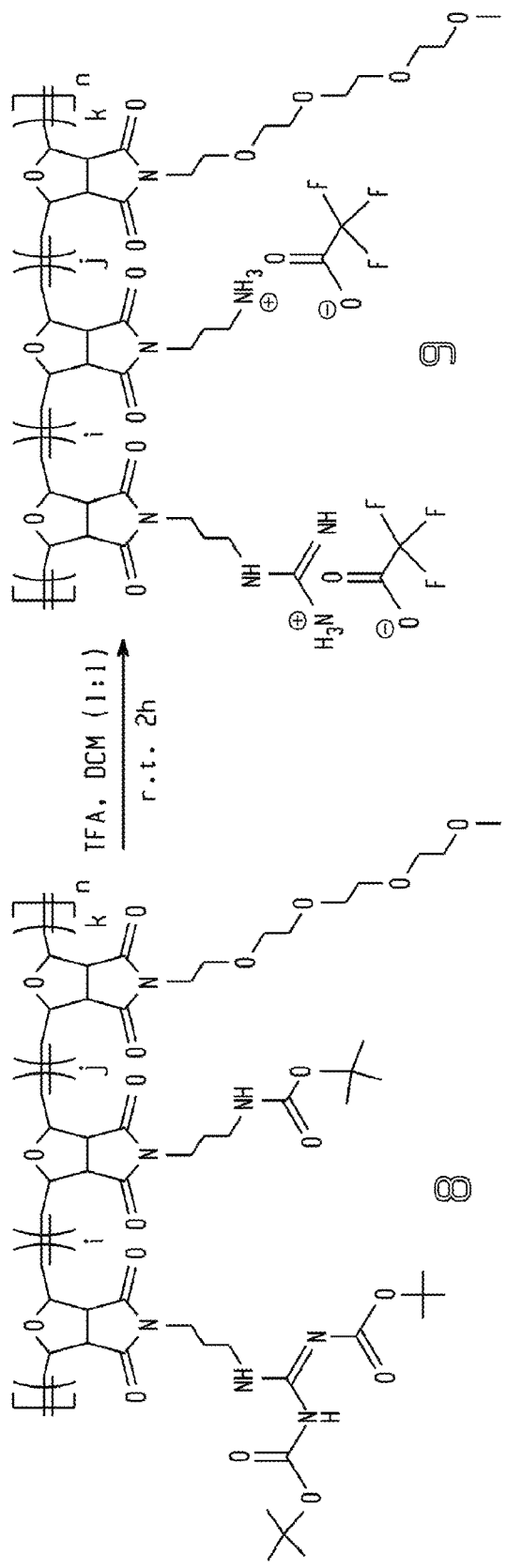
FIG. 6 is a chemical scheme illustrating the synthesis of polymer 9.

Polymer 9, shown in FIG. 6, was synthesized according to the following procedure. To a 50 milliliter round bottom flask equipped with a stir bar was added polymer 8 (400 milligrams). Dichloromethane was purged with nitrogen for five minutes and 12 milliliters was added to the flask, which was then sealed with a septum and purged with nitrogen for five minutes. The main nitrogen line was left in the septum and the nitrogen pressure was reduced to a steady stream. 12 milliliters of trifluoroacetic acid (TFA) (excess) was added and the reaction was allowed to stir for two hours. Excess TFA was removed by rotary evaporation with DCM (3×). The polymer residue was dissolved in a minimal amount of water, filtered through a 0.22 micrometer polyethersulfone (PES) syringe filter and lyophilized to yield polymer 9 as an off-white solid which readily dissolves in water. The molecular weight of polymer 9 was estimated based on the extent of conversion of the polymer to the deprotected form based on $^1$H NMR spectroscopy and the Mw of the starting polymer (polymer 8). Using this method, Polymer 9 was found to have a weight average molecular weight (Mw) of 23,486 Daltons (Da). The polymer was also characterized using $^1$H NMR spectroscopy. $^1$H NMR (400 MHz, D$_2$O) 6.1 (br, 2H), 5.91 (br, 2H), 5.2 (br, 2H), 4.64 (br, 2H), 3.65 (br, 19H), 3.39 (s, 2H), 3.21 (br, 2H), 3.01 (br, 2H), 1.99 (br, 2H), 1.89 (br, 2H).

Polymer Nanocapsule Formation

Figure 7:
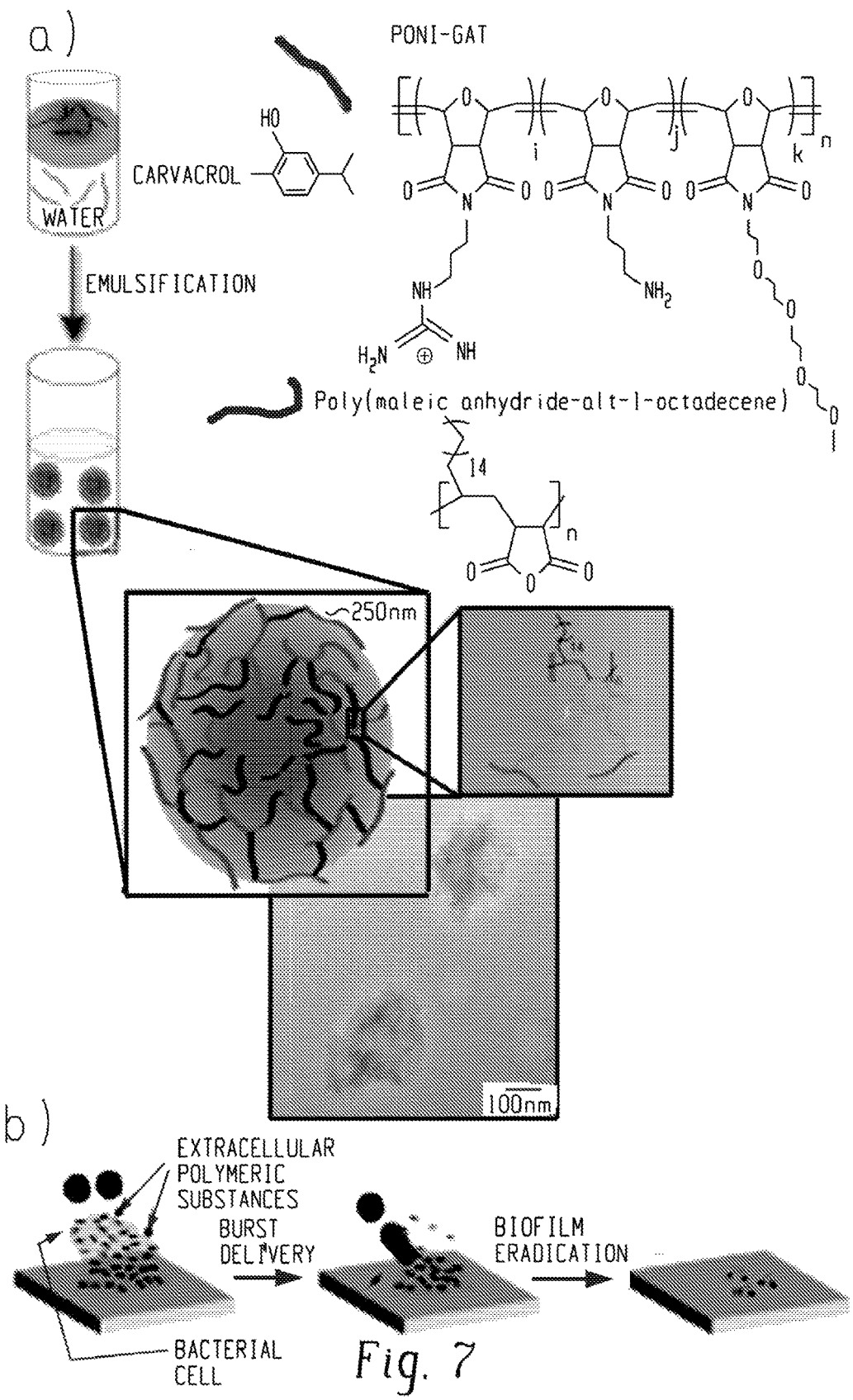
FIG. 7 is a schematic illustration depicting the formation of polymer nanocapsules (a) and delivery of the nanocapsules to a biofilm, resulting in biofilm eradication (b).

Polymer nanocapsules were prepared according to the following procedure, as depicted in FIG. 7. A typical cross-linked polymer nanocapsule was prepared by weighing out 500 milligrams of the commercially available Poly(maleic anhydride-alt-1-octadecene)(p-MA-OC) (available from Sigma), and dissolving it in 4.5 grams of carvacrol (available from Sigma, CAS Reg. No. 499-75-2) to obtain a polymer loading of 10 wt. % (based on the total weight of the p-MA-OC and the carvacrol). This o-MA-OC/carvacrol mixture can be referred to as the "crosslinking oil". Polymer loadings of 0, 1, 3, 5, and 7 wt. % were also tested. Next, in a 600 µl Eppendorf tube, 3 µl of the crosslinking oil was added. Polymer 9 (20 µl of a 150 micromolar (polymer concentration) solution) was added, followed by 477 µl of milliQ water, which was previously adjusted to a pH of 10.0. The pH adjustment is necessary to ensure high reactivity of the amines towards the crosslinking oil. This mixture was shaken using an amalgamator (LINEA TAC, Model: 400M) for 50 seconds on high speed (e.g., at 4200 rpm). The resulting capsules were allowed to sit for at least several hours (e.g., 3 hours) to promote complete crosslinking. In some instances, the capsules were left for 12 to 18 hours to ensure complete crosslinking.

Polymer Nanocapsule Characterization

The polymer nanocapsules were characterized using dynamic light scattering (DLS), transmission electron microscopy (TEM), scanning electron microscopy (SEM), attenuated total reflectance Fourier transform infrared spectroscopy (ATR-FT-IR), and fluorescamine assay to determine various properties including size, dispersity, crosslinking, and permeability of the antimicrobial polymer nanocapsules.

Figure 8:
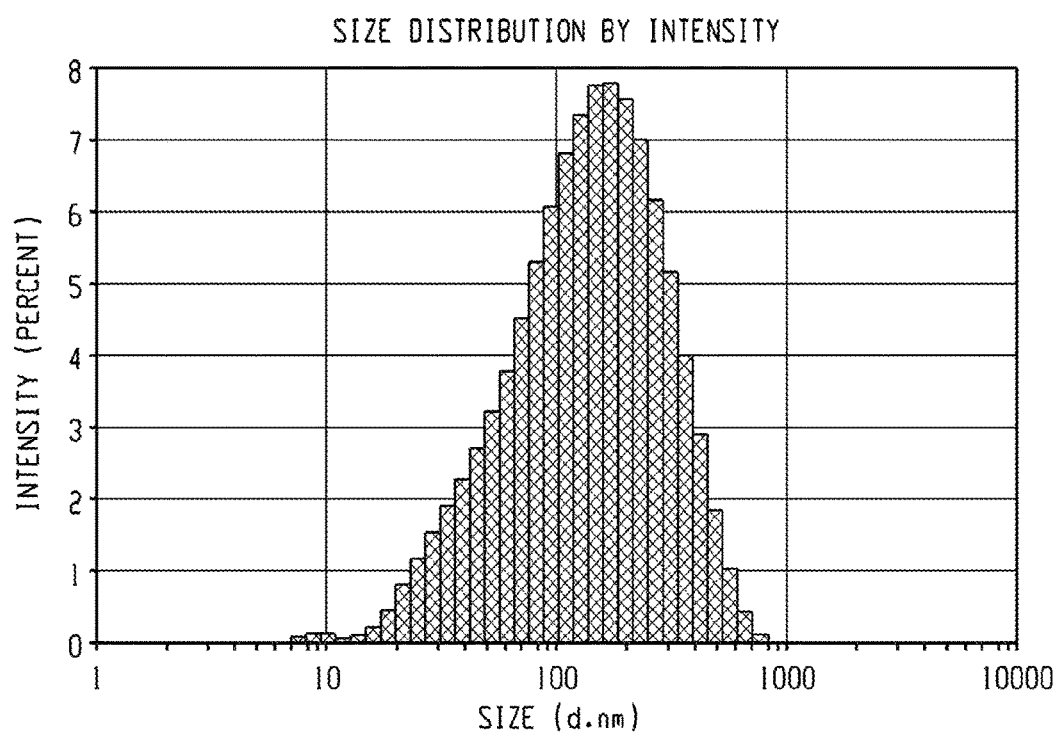
FIG. 8 shows a size histogram (by intensity) obtained by dynamic light scattering (DLS) on a solution of crosslinked polymer nanocapsules having a carvacrol core containing 10 wt. % poly(maleic anhydride-alt-1-octadecene) (p-MA-OC) in phosphate buffered saline solution (150 millimolar).
Figure 9:
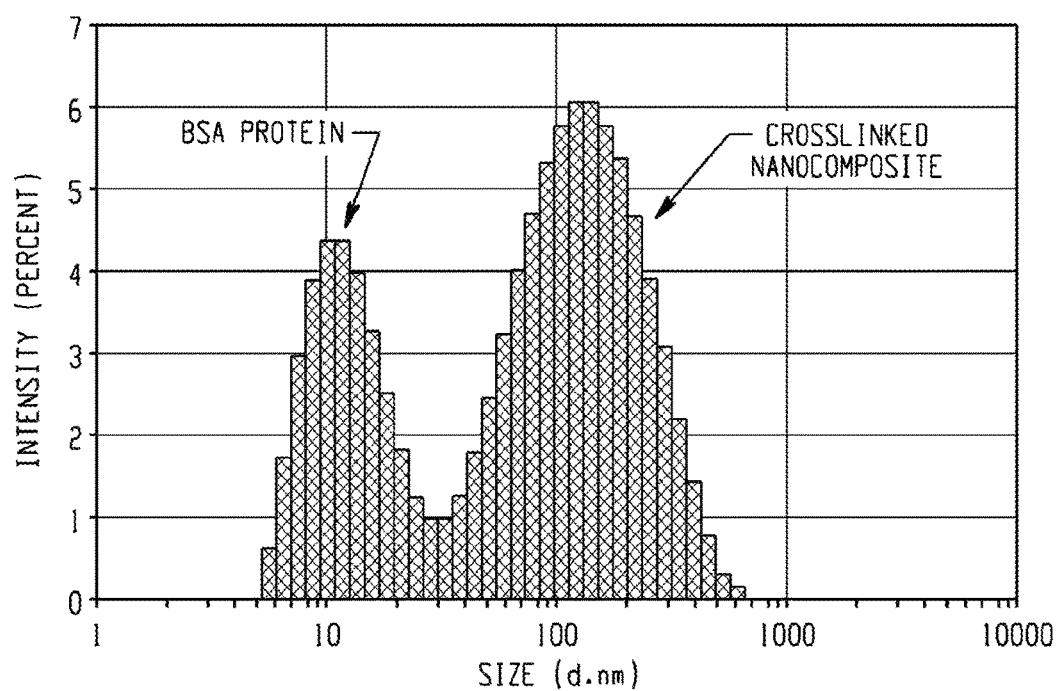
FIG. 9 shows the crosslinked nanocapsules in 10% Fetal Bovine Serum after one hour incubation, determined using dynamic light scattering.
Figure 10:
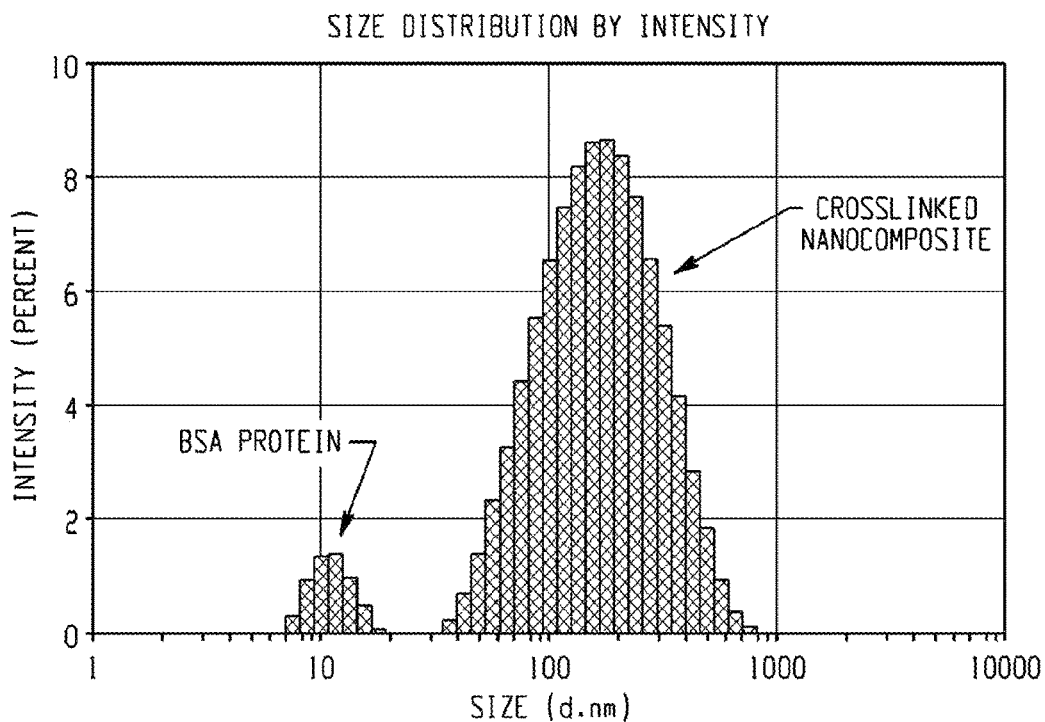
FIG. 10 shows the crosslinked nanocapsules in 10% Fetal Bovine Serum after 48 hours of incubation, determined using dynamic light scattering.

As shown in FIG. 8, the DLS results show capsule size of about 100 nanometers in phosphate buffer (pH 7.4, 150 mM). As shown in FIG. 9, DLS in 10% Fetal Bovine Serum (FBS) after 1 hour of incubation shows a size similar to that observed in PBS. A peak for Bovine Serum Albumin (BSA) was also observed due to the use of FBS in the solution. As shown in FIG. 10, DLS in 10% Fetal Bovine Serum (FBS) after 48 hours of incubation shows a size similar to that observed in PBS and FBS after 1 hour incubation time. These DLS results are indicative of the stability of the polymer nanocapsules in varying media and for prolonged periods of time (e.g., up to 48 hours).

Figure 11:
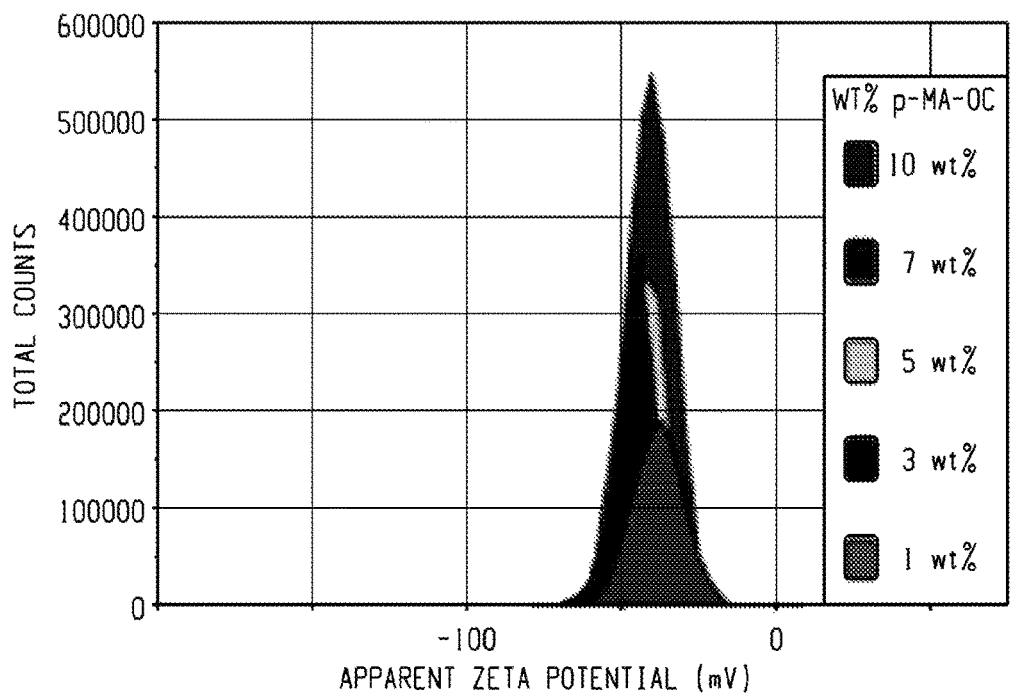
FIG. 11 shows the zeta potential of crosslinked carvacrol-containing polymer nanocapsules prepared from varying concentrations of polymer (P-MA-OC) (1, 3, 5, 7, and 10 wt %).
Figure 12:
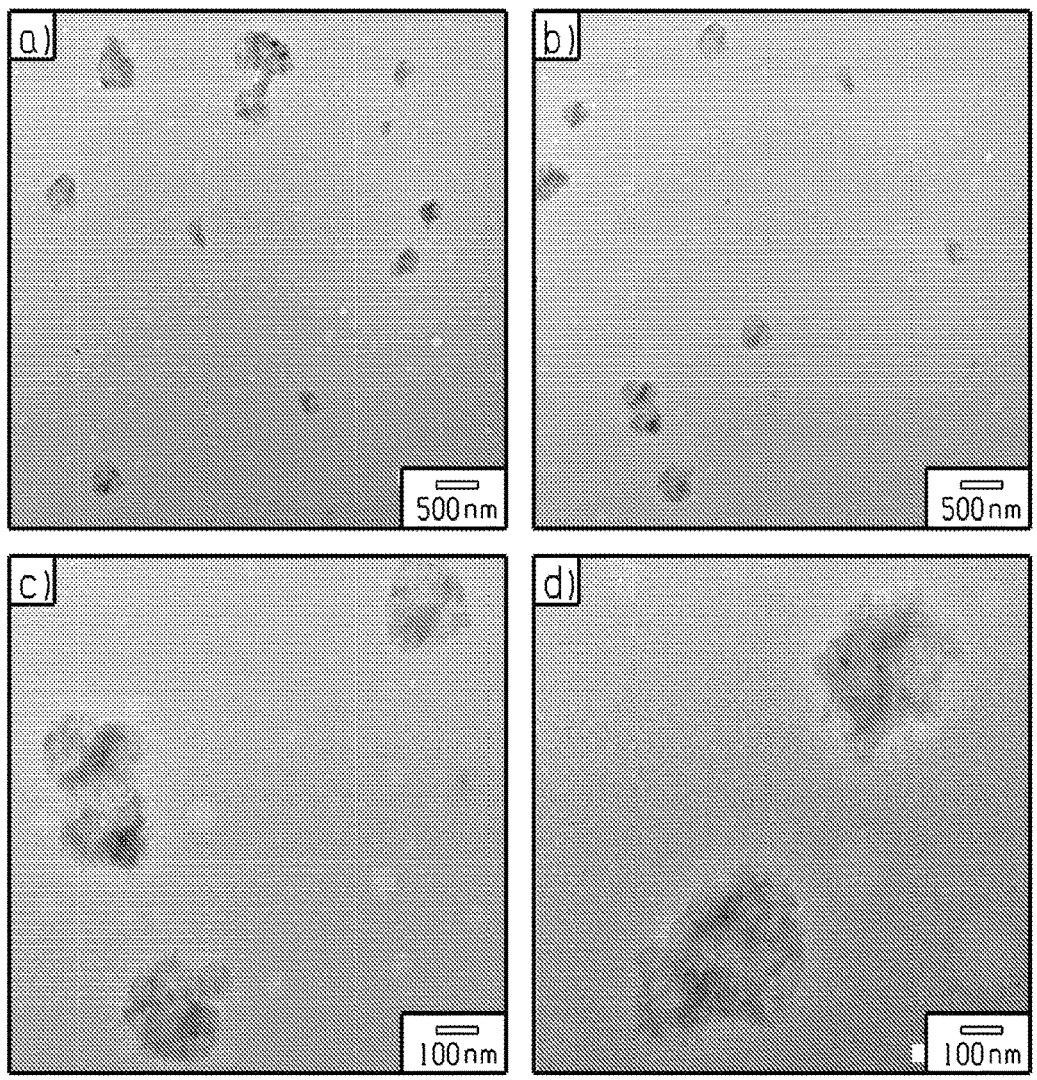
FIG. 12 shows transmission electron micrographs of a film formed from solutions of crosslinked carvacrol-containing polymer nanocapsules, stained with uranyl acetate. The scale bar is 500 nanometers in the micrographs labeled (a) and (b), and the scale bar is 100 nanometers in the micrographs labeled (c) and (d).
Figure 13:
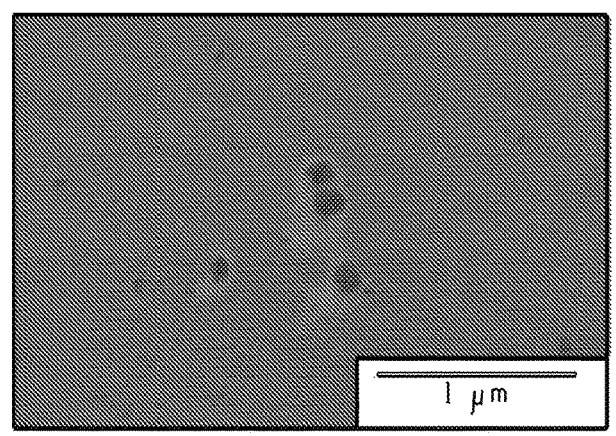
FIG. 13 shows a scanning electron micrograph of a film formed from a solution of crosslinked carvacrol-containing polymer nanocapsules. The scale bar is 1 micrometer.
Figure 14:
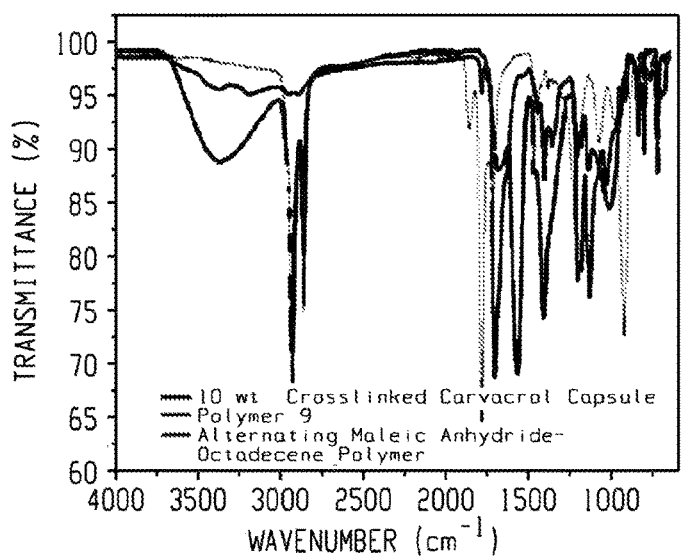
FIG. 14 shows the attenuated total reflectance Fourier transform infrared spectra of crosslinked capsules, polymer 9, and p-MA-OC.

Zeta potential measurements were also performed on the crosslinked nanocapsules and the zeta potential was found to by −42 mV, as shown in FIG. 11. Furthermore, as shown in FIG. 14, varying the concentration of the polymer used to prepare the nanocapsules (i.e., from 1, 3, 5, 7, and 10 weight percent) did not substantially affect the observed zeta potential of the resulting capsules. Capsules containing higher percentages of p-MA-OC shifted slightly toward more negative zeta potentials, likely due to the increased presence of a carboxylate group from the p-MA-OC. Without wishing to be bound by theory, it is believed that the polymer amines are reacting with the maleic anhydride units to form the corresponding amides and carboxylic acids or carboxylates. The carboxylates are believed to cause the negative zeta potential observed for the crosslinked polymer nanocapsules. TEM analysis (FIG. 12) showed capsules with an average size of 100 nanometers, which supports the DLS result as the hydrodynamic diameter would be expected to by slightly larger in solution. The TEM image was obtained using an accelerating voltage of 200 electron volts, and staining with uranyl acetate. Scanning electron microscopy (SEM) was also performed, and the results are provided in FIG. 13.

Figure 15:
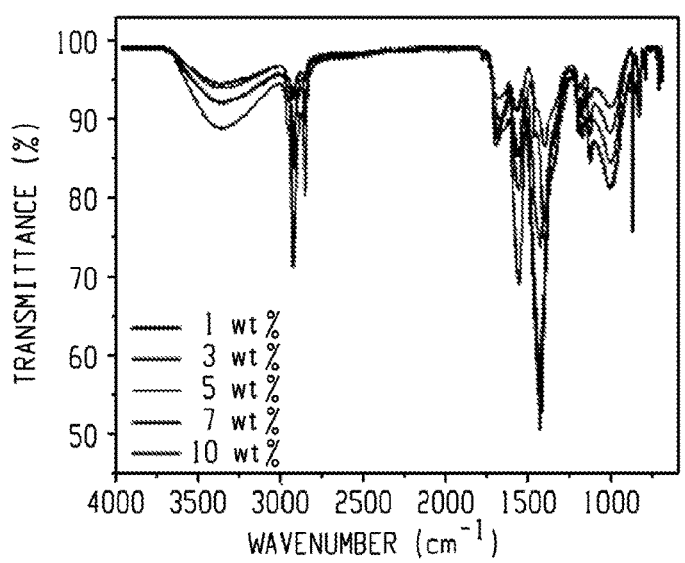
FIG. 15 shows the attenuated total reflectance Fourier transform infrared spectra of crosslinked capsules prepared from capsules having a core containing p-MA-OC in an amount of 1 to 10 wt. % based on the total weight of the core.

ATR-FT-IR was performed on polymer 9, p-MA-OC, and the crosslinked capsules prepared from a core containing 10 wt. % p-MA-OC. As shown in FIG. 14, analysis of the crosslinked capsules showed the disappearance of the maleic anhydride frequencies (1,857 cm$^{-1}$, 1776 cm$^{-1}$), appearance of amide functionality (1,650 cm$^{-1}$), and appearance of carboxylate salts (1,564 cm$^{-1}$). In addition, as shown in FIG. 15, all wt. % additions of p-MA-OC ranging from 1 to 10 wt. % used to make crosslinked nanocapsules showed the same frequencies found with the 10 wt. % crosslinked capsules, as described above, confirming their utility in preparing similar crosslinked nanocapsules having varying crosslink densities.

Figure 16:
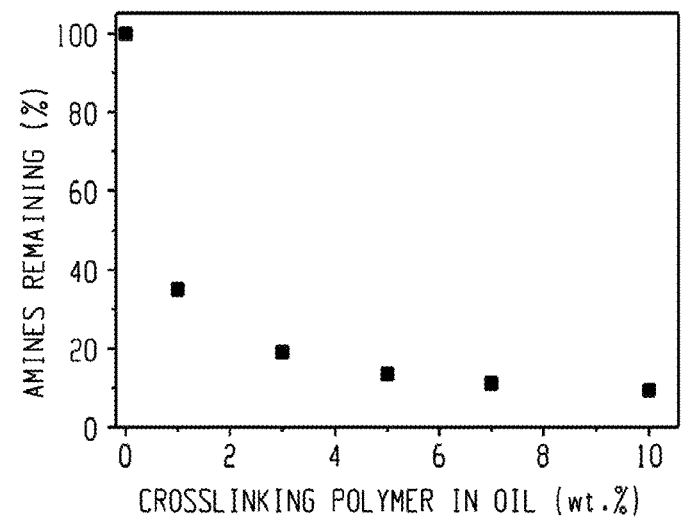
FIG. 16 shows the dependence of the crosslinking on the weight percent of the crosslinking polymer (p-MA-OA) in the oil core, determined using a fluorescence assay, monitoring the percentage of free amines.
Figure 17A:
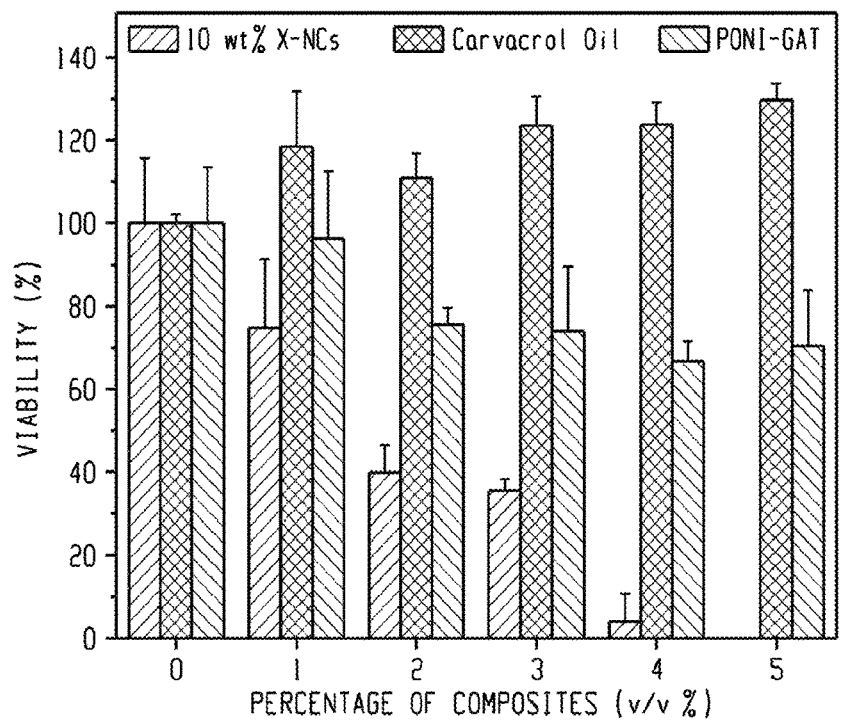
FIG. 17 shows the cell viability of a bacterial biofilm after treatment with crosslinked polymer nanocapsules (10 weight percent), carvacrol oil, and PONI-GAT at varying concentrations for a) CD-2 (*E. Coli*), b) CD-489-MRSA (*S. aureus*), c) CD-1006 (*P. aeruginosa*), and d) CD-1412 (*En. cloacae*) biofilms. Incubation of the biofilms was done for three hours.
Figure 17B:
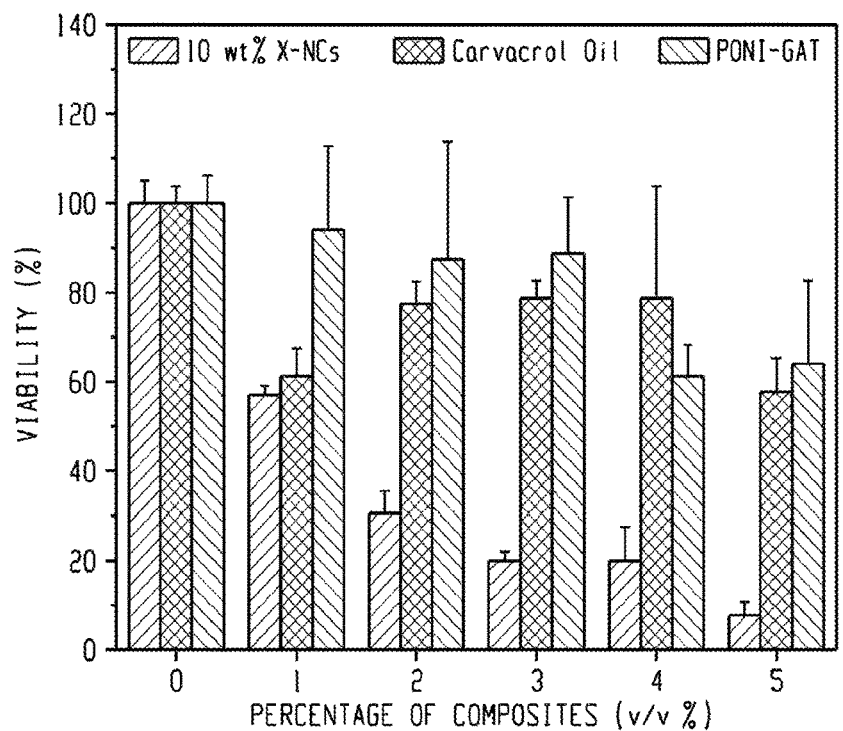
Figure 17C:
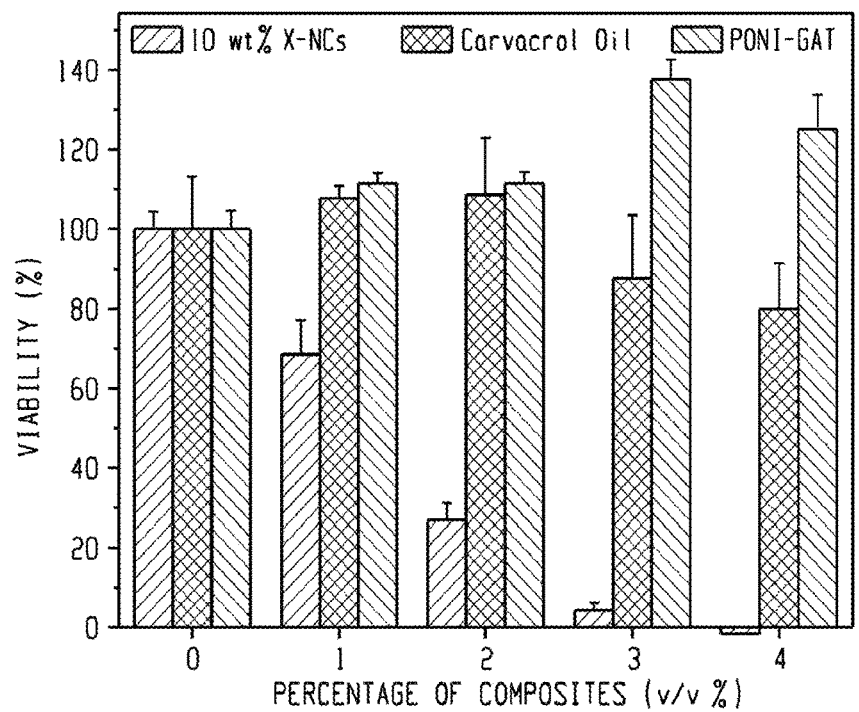
Figure 17D:
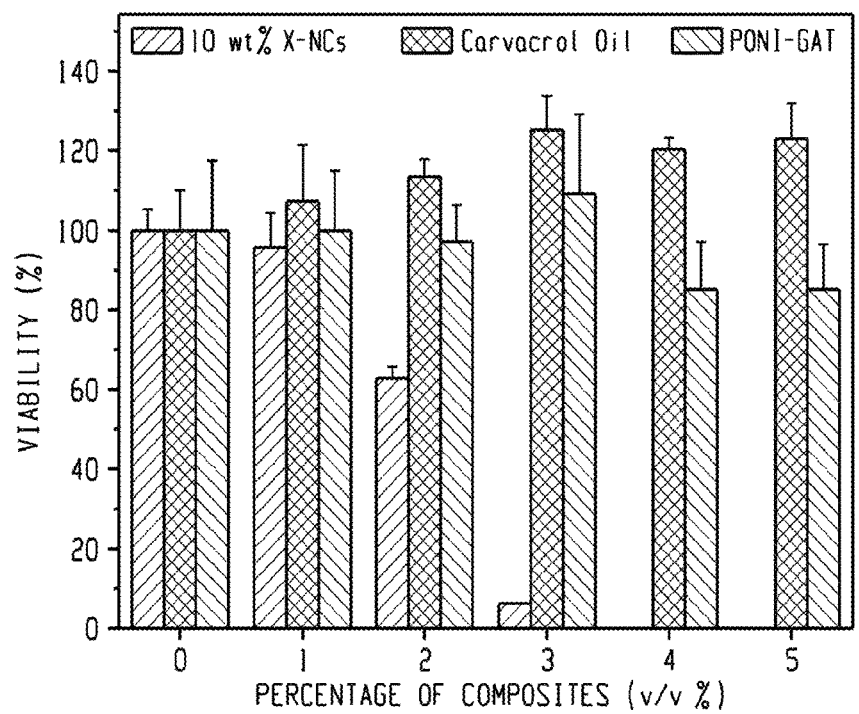

To determine the degree of crosslinking, a fluorescamine assay was performed to determine the number of remaining amines post-crosslinking. After formation of the crosslinked nanocapsules, 500 µl of the nanocapsule solution was added to 450 µl of 5 millimolar phosphate buffer having a pH of 7.4 and 50 µl of a 2 milligram per milliliter solution of fluorescamine in acetonitrile. The solution was sonicated for 10 minutes. 500 µl was then removed and diluted with 500 µL of ethanol. The fluorescence at 475 nanometers was monitored for each crosslinked sample (e.g., having 1, 3, 5, 7, or 10 wt. % p-MA-OC). The results shown in FIG. 16 indicate that as the amount of p-MA-OC in the carvacrol oil is increased, the percentage of remaining amines decrease exponentially.

Biofilm Formation

*Pseudomonas Aeruginosa* bacteria were inoculated in LB broth obtained from Fisher BioReagents at 37° C. overnight. The bacterial cultures were then harvested by centrifugation and washed with 0.85% aqueous sodium chloride solution three times. Concentrations of resuspended bacterial solution were determined by optical density measured at 600 nanometers. Seeding solutions were then made in minimal M9 broth obtained from Teknova to reach an optical density of 0.1 determined at 600 nanometers. 100 µl of the seeding solutions were added to each well of the microplate. M9 medium without bacteria was used as negative control. The plates were covered and incubated at room temperature under static conditions for a desired period. Planktonic bacteria were removed by washing with phosphate buffered saline (PBS) three times.

Treatment of Bacterial Biofilms

Capsule solutions and the respective controls were prepared at different concentrations (0 to 4 volume percent) in M9 medium and these solutions were then added to the one-day old *P. aeruginosa* biofilm. Biofilms were treated for one day at room temperature and then washed with PBS for three times. After washing, alamar blue solution in PBS was added and the plate was incubated at 37° C. for two hours. After incubation the plates were measured in a plate reader at 560 nm/590 nm (ex/em). M9 medium without bacteria was used as a negative control.

Figure 18:
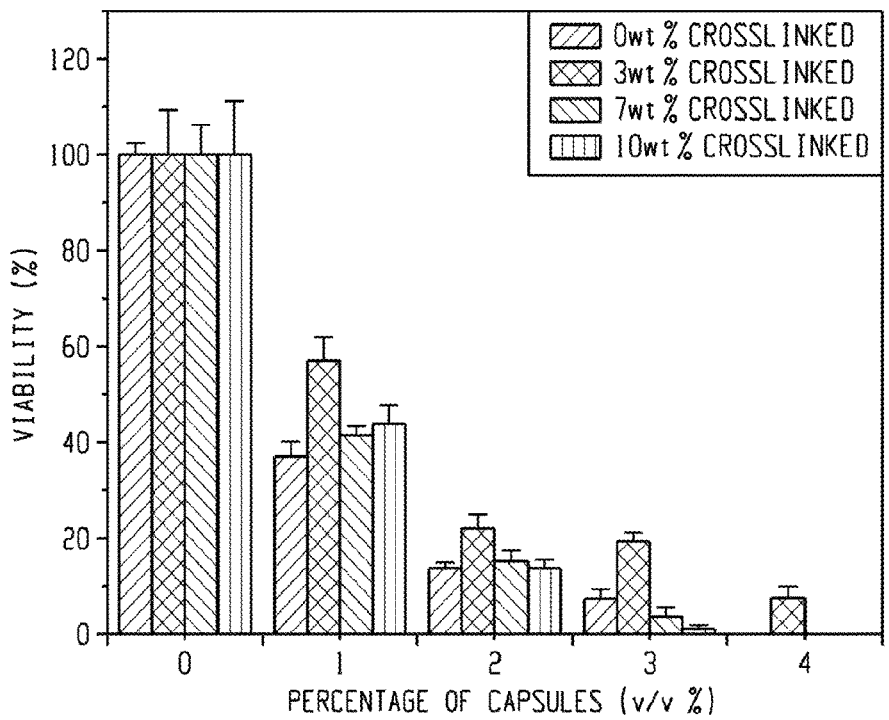
FIG. 18 shows the cell viability of a bacterial biofilm after treatment with crosslinked polymer nanocapsules prepared from a core comprising 0 (noncrosslinked), 3, 7, and 10 weight percent crosslinking polymer 9 in carvacrol oil.
Figure 19:
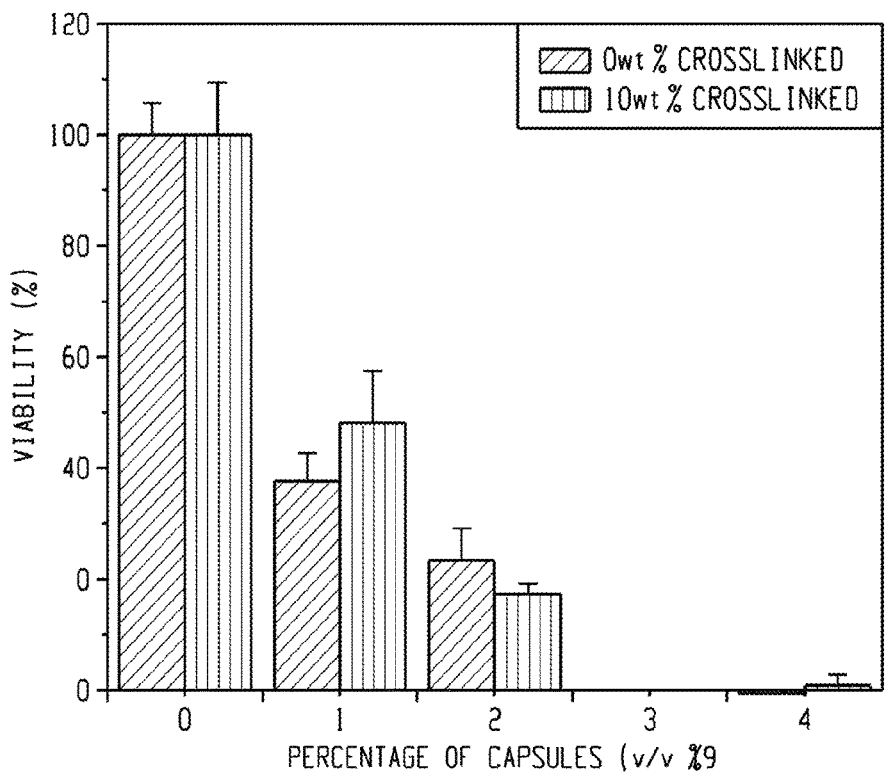
FIG. 19 shows the cell viability of a bacterial biofilm after treatment with crosslinked polymer nanocapsules and non-crosslinked polymer nanocapsules.
Figure 20:
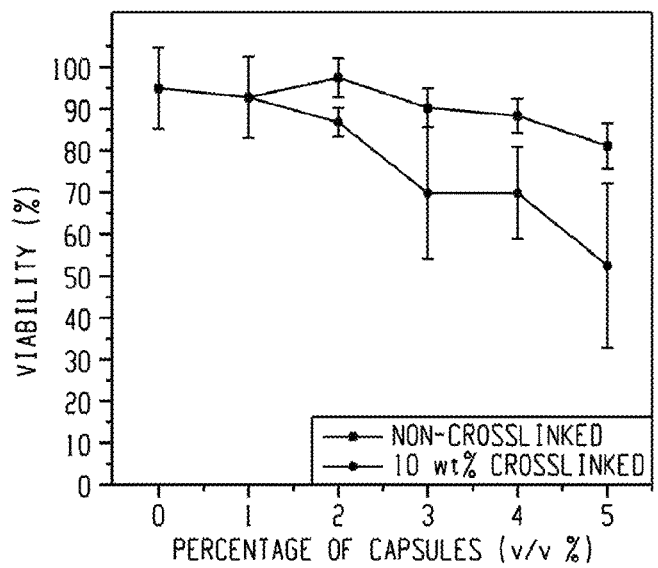
FIG. 20 shows the viability of 3T3 Fibroblast cells after 3 hours of incubation.

As shown in FIG. 17, crosslinked polymer nanocapsules prepared from a core containing 10 wt. % p-MA-OC in carvacrol oil exhibited toxicity to the bacterial biofilm at reduced concentrations compared to the carvacrol oil alone, as well as a 10 wt. % solution of p-MA-OC in carvacrol oil. Polymer 9 itself was also observed to be non-toxic to the bacterial biofilm. These results demonstrate that the nanocapsules disclosed herein can advantageously be used for effective delivery of an essential oil (e.g., carvacrol oil) as a potent antimicrobial. As shown in FIG. 18, capsules prepared from varying concentrations of the crosslinking polymer 9 also are useful in the treatment of the biofilms. FIG. 19 shows the comparison of crosslinked and noncrosslinked polymer nanocapsules for the treatment of the biofilm. Both the crosslinked and noncrosslinked polymer nanocapsules exhibited similar cytotoxicities towards the bacterial biofilm.

Figure 21:
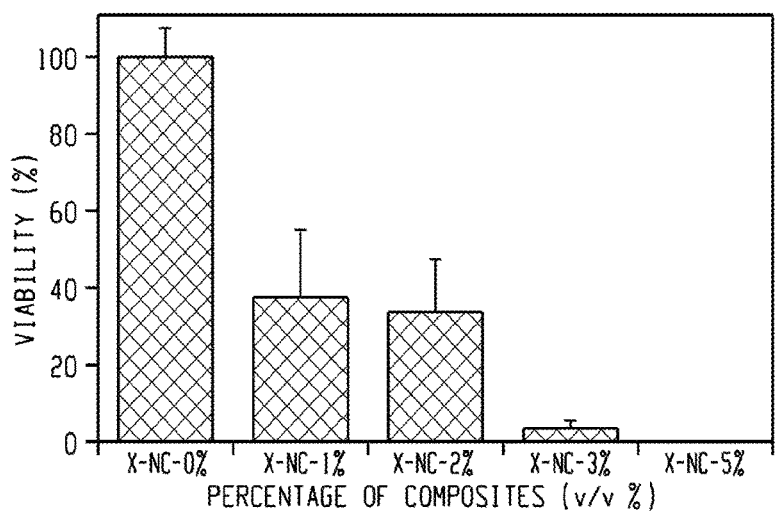
FIG. 21 shown the viability of a resistant $20^{th}$ generation bacterial biofilm from (CD-2, *E. Coli*) after three hours of incubation with varying concentrations of polymer nanocapsules: 0 (control), 1, 2, 3, and 5%.

As shown in FIG. 21, the polymer nanocapsules could also effectively kill a resistant $20^{th}$ generation bacterial biofilm (CD-2, *E. Coli*) after three hours of incubation.

Biofilm-3T3 Fibroblast Cell Coculture

Figure 22:
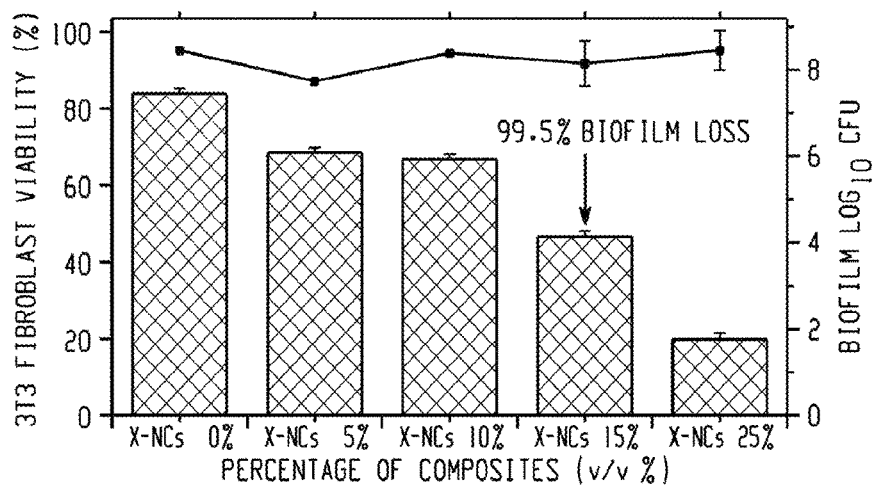
FIG. 22 shows the co-culture after three hours of an ATCC-19660 *Pseudomonas aeruginosa* biofilm and 3T3 Fibroblast Cells with varying percentages of the crosslinked nanoparticles: 0 (control), 5, 10, 15, and 25%).

A total of 20,000 NIH 3T3 (ATCC CRL-1658) cells were cultured in Dulbecco's modified Eagle medium (DMEM; ATCC 30-2002) with 10% bovine calf serum and 1% antibiotics at 37° C. in a humidified atmosphere of 5% CO2. Cells were kept for 24 hours to reach a confluent monolayer. Bacteria (P. aeruginosa) were inoculated and harvested. Afterwards, seeding solutions were made in buffered DMEM supplemented with glucose to reach an OD600 of 0.1. Old medium was removed from 3T3 cells followed by addition of 100 µL of seeding solution. The cocultures were then stored in a box with damp paper towels at 37° C. overnight without shaking. Testing solutions at different concentrations were made by diluting nanocapsules into DMEM prior to use. Media was removed from coculture, replaced with testing solutions, and incubated for 3 hours at 37° C. Cocultures were then analyzed using a LDH cytotoxicity assay to determine mammalian cell viability. The coculture viability results are shown in FIG. 22. To determine the bacteria viability in biofilms, the testing solutions were removed and cocultures were washed with PBS. Fresh PBS was then added to disperse remaining bacteria from biofilms in coculture by sonication for 20 min and mixing with pipet. The solutions containing dispersed bacteria were then plated onto agar plates and colony forming units were counted after incubation at 37° C. overnight.

Crosslinked, Degradable Polymer Nanocapsules

Figure 23:
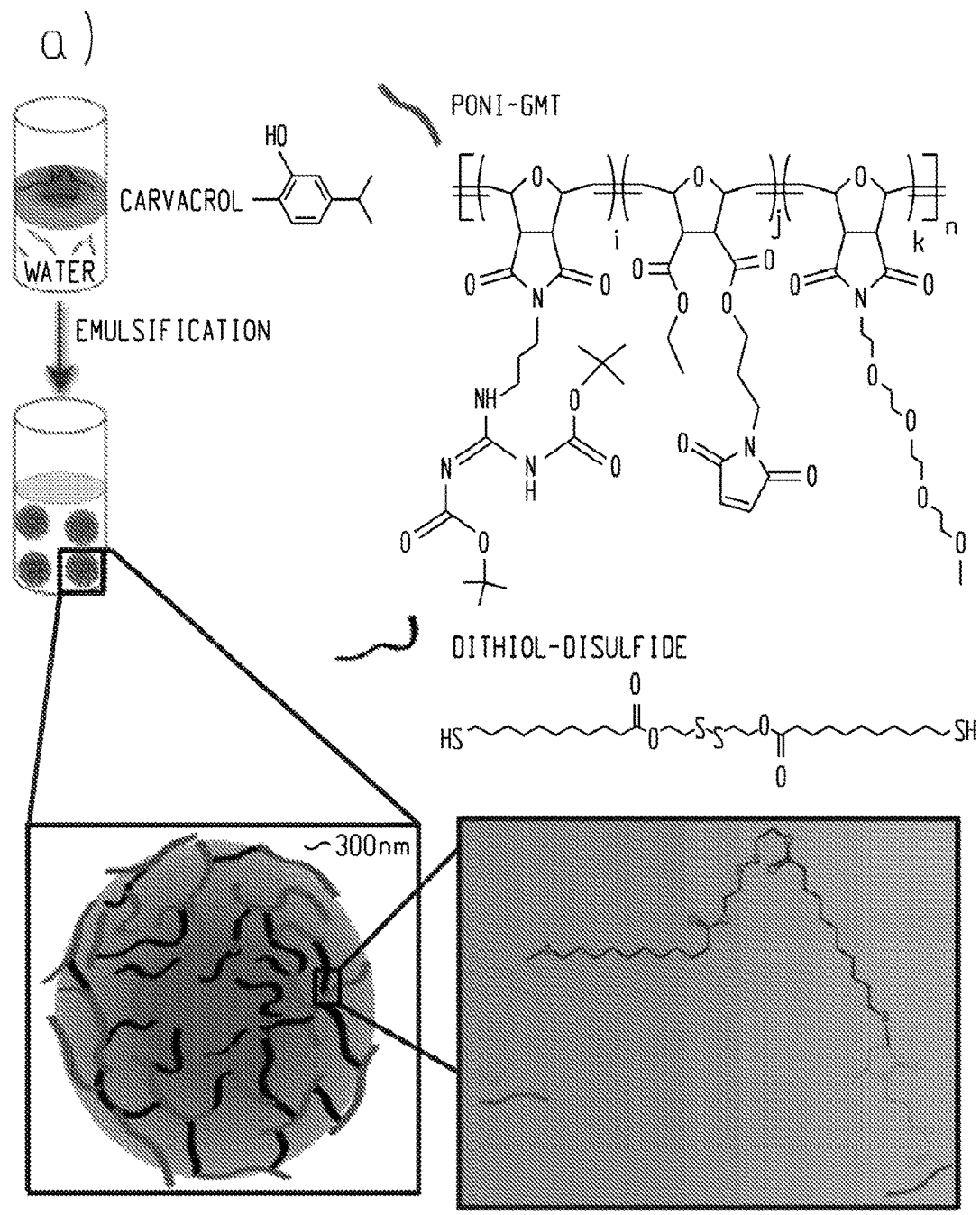
FIG. 23 is a schematic illustration depicting the formation of degradable polymer nanocapsules prepared from a maleimide-containing polymer ("PONI-GMT") which can be crosslinked using a dithiol-disulfide.
Figure 24:
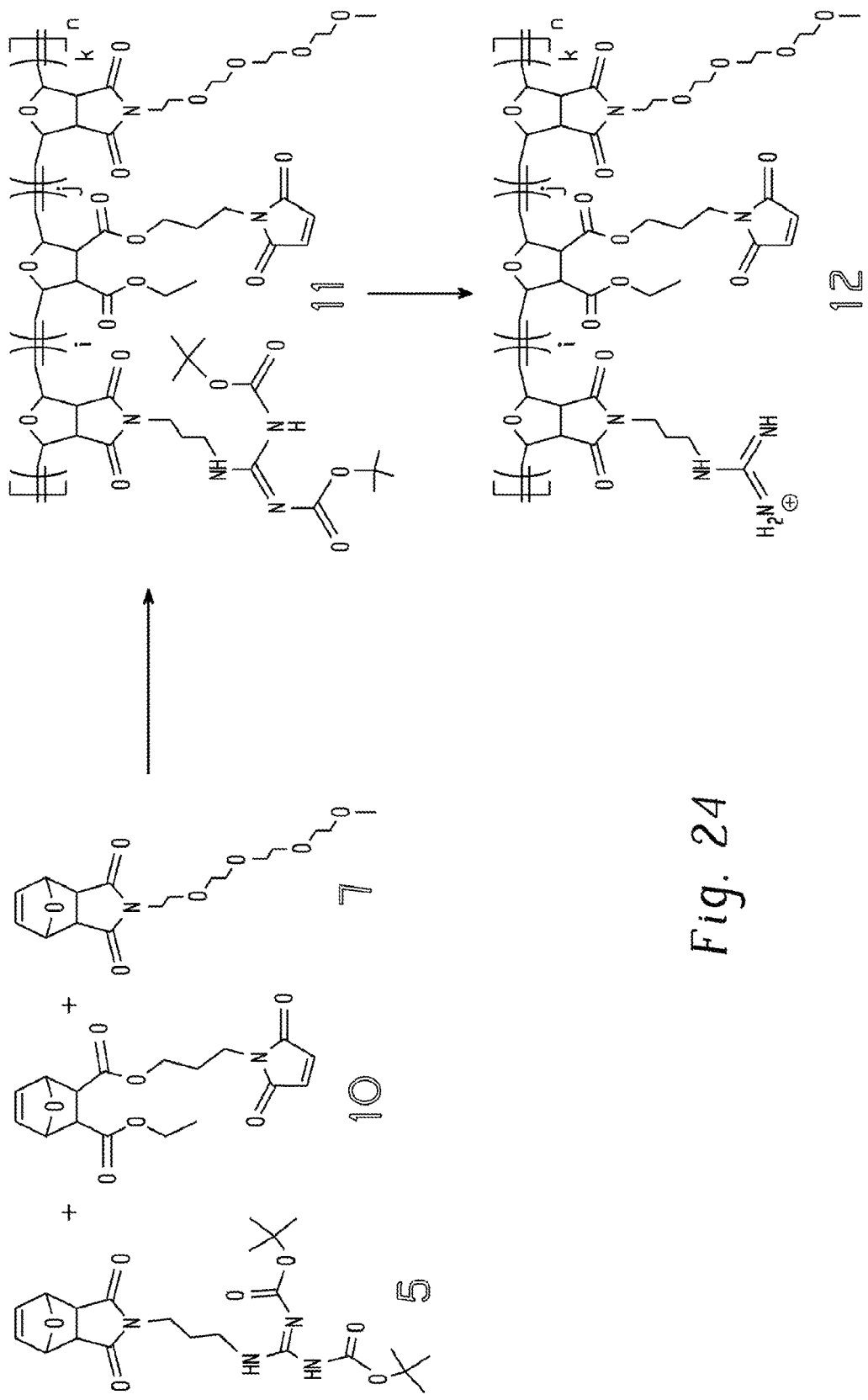
FIG. 24 is a chemical scheme illustrating the synthesis of polymers 11 and 12.

A schematic illustration of crosslinkable, degradable polymer nanocapsules in shown in FIG. 23. The maleimide-containing polymer ("PONI-GMT"), shown as Polymer 12 in FIG. 24, was prepared according to the following procedure.

To a 10 milliliter pear-shaped air-free flask equipped with a stir bar was added Compound 5 (266 milligrams, 0.57 millimoles, 0.4 equivalents), Compound 7 (254 milligrams, 0.715 millimoles, 0.5 equivalents), Compound 10 (50 milligrams, 0.14 millimoles, 0.1 equivalent), and 4 milliliters of dichloromethane (DCM). In a separate 10 milliliter pear-shaped air-free flask was added Grubbs $3^{rd}$ generation catalyst (15 milligrams, 0.017 millimoles, 0.012 equivalents) and 1 milliliters DCM. Both flasks were sealed with septa and attached to a schlenk nitrogen/vaccum line. Both flasks were freeze-pump-thawed three times. After thawing, Grubbs $3^{rd}$ generation catalyst solution was syringed out and quickly added to the flask containing the monomers, and allowed to react for 12 minutes. After the allotted time, ethyl vinyl ether (200 µL) was added and allowed to stir for 15 minutes. The reaction mixture was then diluted to two times the volume and precipitated into a heavily stirred solution of ether:hexane (150 milliliters, 1:1 volume ratio) to yield Polymer 11. MW=46,157, PDI=1.45, as determined by THF GPC using a polystyrene calibration curve). $^1$H NMR (500 MHz, CDCl$_3$) 11.49 (s, 2H), 8.45 (br, 2H), 6.71 (br, 0.8H), 6.09 (br, 4H), 5.8 (br, 6H), 5.05 (br, 6H), 4.5 (br, 4H), 3.65 (br, 52H), 3.45 (br, 2H), 3.35 (s, 7H), 3.33 (br, 2H), 1.89 (br, 4H), 1.8 (br, 4H), 1.49 (s, 20H), 1.2 (br, 2H).

Polymer 12 was prepared from Polymer 11. To a 50 milliliter round bottom flask equipped with a stirbar was added Polymer 11 (400 milligrams). DCM was purged with nitrogen for five minutes and 12 milliliters was added to the flask, sealed with a septum and purged with nitrogen for five minutes. The main nitrogen line was left in the septum and the nitrogen pressure was reduced to a steady stream. 12 milliliters of trifluoroacetic acid (TFA) (excess) was added and the reaction was allowed to stir for two hours. Afterwards, excess TFA was removed by rotovaping with DCM (3×). The reaction residue was dissolved in a minimal amount of water, filtered through a polyethersulfone (PES) syringe filter and lyophilized to yield polymer 12 as a white solid which readily dissolves in water. MW ~33,157, as determined using GPC. $^1$H NMR (400 MHz, D$_2$O) 6.7 (br, 0.4H), 5.94 (br, 4H), 5.74 (br, 4H), 4.82 (br, 4H), 4.45 (br, 4H), 3.5 (br, 40H), 3.2 (s, 6H), 3.02 (br, 4H), 1.7 (br, 4H), 1.05 (br, 2H).

Polymer nanocapsules were prepared from polymer 12 ("PONI-GMT") using the same procedure as described above. A dithiol-disulfide was added to the carvacrol oil in an amount of 3 weight percent, based on the weight of the oil phase.

Figure 25A:
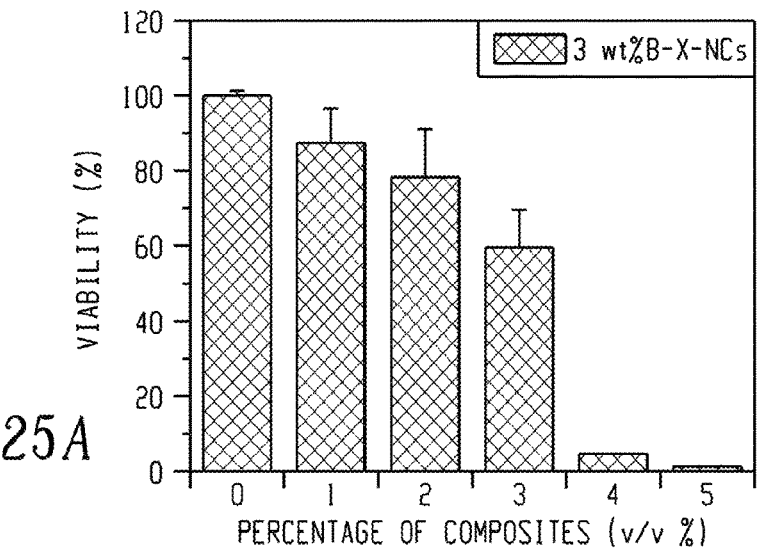
FIG. 25 shows the cell viability of (a) ATCC 19660 Non-pathogenic *P. aeruginosa*, (b) CD-1006 Pathogenic *P. aeruginosa*, and (c) CD-1412 *E. cloacae* complex after 3 hours of incubation with degradable polymer nanocapsules.
Figure 25B:
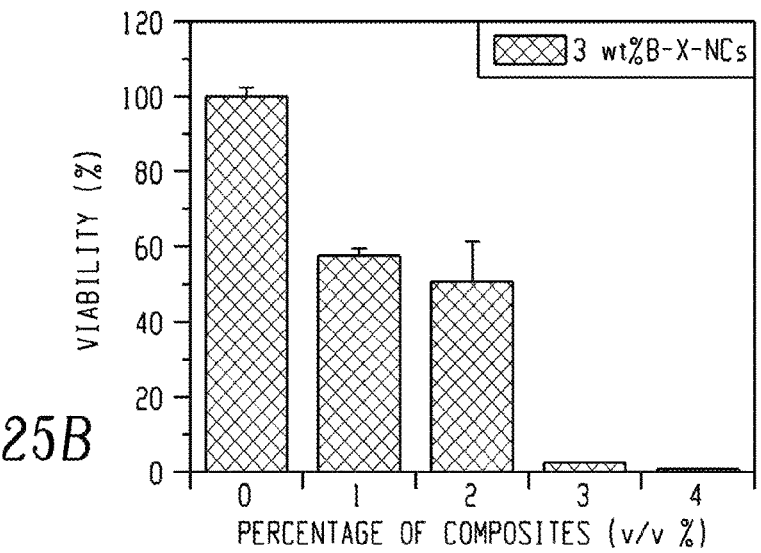
Figure 25C:
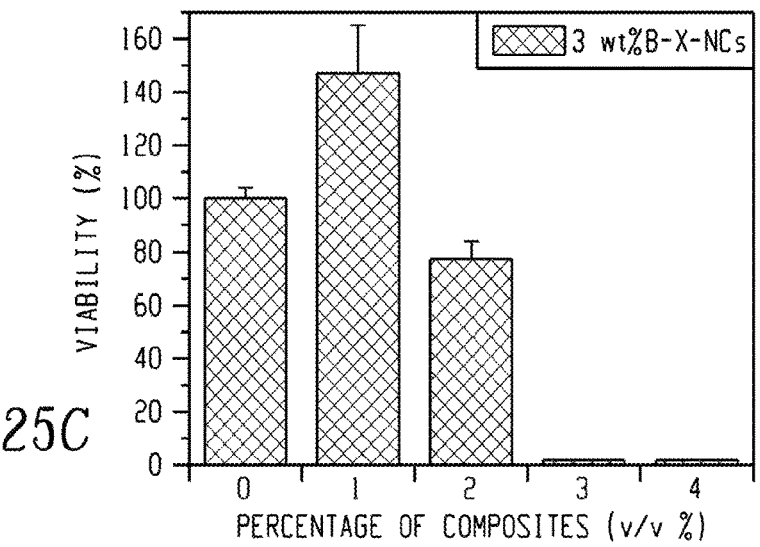

The crosslinked nanocapsules were evaluated for efficacy against bacterial biofilms using a similar protocol as described above. Three biofilms were tested (ATCC19660 Non-pathogenic P. aeruginosa, CD-1006 Pathogenic P. aeruginosa, and CD-1412 E. cloacae complex), and the viability of each biofilm was assessed after three hours of incubation with the nanocapsules at varying nanocapsule concentrations. As shown in FIG. 25, the nanocapsules were shown to be toxic to the biofilms after three hours of incubation.

The nanocapsules, dispersions, and methods of the present disclosure include at least the following embodiments.

Embodiment 1

A nanocapsule comprising, a liquid hydrophobic core comprising an essential oil; and a shell encapsulating the core, the shell comprising a copolymer comprising repeating units of Formula (I) and (II)
wherein X is independently at each occurrence —O—, —S—, —CH$_2$—, —(CR$^4$R$^5$)—, or

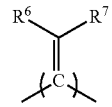

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 1 to 10, a divalent a C$_{1-20}$ alkylene oxide group, or a divalent poly(C$_{1-6}$ alkylene oxide) group; R$^1$ is independently at each occurrence hydrogen, a C$_{1-12}$ alkylene group, or a —C(=O)—O—(C$_{1-6}$ alkyl) group; y is 2 or 3; p is 0 or 1; and R$^2$ is independently at each occurrence a C$_{1-12}$ alkylene group, a C$_{6-20}$ arylene group, a C$_{1-20}$ alkylene oxide group, a poly(C$_{1-6}$ alkylene oxide) group, or a zwitterionic group.

Embodiment 2

The nanocapsule of embodiment 1, wherein the copolymer further comprises repeating units of Formula (III) wherein X is independently at each occurrence —O—, —S—, —CH$_2$—, —(CR$^4$R$^5$)—, or

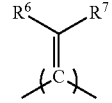

wherein $R^4$ and $R^5$ are independently at each occurrence a $C_{1-6}$ alkyl group and $R^6$ and $R^7$ are independently at each occurrence hydrogen or a $C_{1-6}$ alkyl group; $L^2$ is independently at each occurrence a divalent group that is ($-CH_2-$)$_z$, wherein z is an integer from 1 to 10, a divalent a $C_{1-20}$ alkylene oxide group, or a divalent poly($C_{1-6}$ alkylene oxide) group; $R^3$ is independently at each occurrence hydrogen, a $C_{1-12}$ alkylene group, or a $-C(=O)-O-(C_{1-6}$ alkyl) group; a is 2 or 3; and b is 0 or 1.

Embodiment 3

The nanocapsule of embodiment 1 or 2, wherein the core further comprises a hydrophobic anhydride-containing polymer in an amount of 0.01 to 15 weight percent, based on the weight of the core.

Embodiment 4

The nanocapsule of embodiment 3, wherein the hydrophobic anhydride-containing polymer comprising repeating units of Formula (VI)
wherein $R^8$ is independently at each occurrence a hydrogen, a $C_{1-20}$ alkyl group or a $C_{6-20}$ aryl group.

Embodiment 5

The nanocapsule of embodiment 3 or 4, wherein at least a portion of the shell is crosslinked with the anhydride-containing polymer.

Embodiment 6

The nanocapsule of any of embodiments 1 to 5, wherein the essential oil is selected from the group consisting of peppermint oil, oregano oil, thymol, menthol, methyl salicylate, eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, or a combination thereof.

Embodiment 7

The nanocapsule of any of embodiments 1 to 6, wherein the essential oil comprises carvacrol oil, limonene, or a combination thereof.

Embodiment 8

The nanocapsule of any of embodiments 1 to 7, wherein the nanocapsule has a diameter of 1 to 500 nanometers.

Embodiment 9

The nanocapsule of any of embodiments 2 to 8, wherein the copolymer comprises 5 to 50 mole percent repeating units of Formula (I); 10 to 50 mole percent repeating units of Formula (II); and 25 to 45 mole percent repeating units of Formula (III); wherein mole percent of each component is based on the total moles of the copolymer.

Embodiment 10

The nanocapsule of any of embodiments 1 to 9, wherein X is —O—.

Embodiment 11

The nanocapsule of any of embodiments 1 to 10, wherein $L^1$ is propylene.

Embodiment 12

The nanocapsule of any of embodiments 1 to 11, wherein $R^1$ is hydrogen.

Embodiment 13

The nanocapsule of any of embodiments 1 to 12, wherein y is 3 and p is 1.

Embodiment 14

The nanocapsule of any of embodiments 1 to 13, wherein $R^2$ is a $C_{1-20}$ alkylene oxide group.

Embodiment 15

The nanocapsule of any of embodiments 1 to 14, wherein $R^2$ is a group having the structure

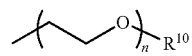

wherein n is 1, 2, 3, or 4; and $R^{10}$ is hydrogen, methyl, or a $C_{1-6}$ alkylamino group, preferably methyl.

Embodiment 16

The nanocapsule of any of embodiments 2 to 15, wherein $R^3$ is hydrogen.

Embodiment 17

The nanocapsule of any of embodiments 2 to 16, wherein $L^2$ is propylene.

Embodiment 18

The nanocapsule of any of embodiments 2 to 17, wherein a is 3 and b is 1.

Embodiment 19

The nanocapsule of any of embodiments 1 to 18, wherein the copolymer has a number average molecular weight of 3,000 to 100,000 Daltons.

Embodiment 20

The nanocapsule of any of embodiments 1 to 19, comprising 90 to 99.9 weight percent of the core; and 0.1 to 10 weight percent of the shell; wherein weight percent is based on the total weight of the nanocapsule.

Embodiment 21

The nanocapsule of any of embodiments 1 to 20, wherein the nanocapsule comprises 1 to 10 weight percent, based on the weight of the nanocapsule, of the core comprising carvacrol oil; and 90 to 99 weight percent, based on the weight of the nanocapsule, of the shell comprising the copolymer, wherein each occurrence of X is —O—; each occurrence of $L^1$ is propylene; each occurrence of $R^1$ is hydrogen; each occurrence of y is 3; each occurrence of p is 1; each occurrence of $R^2$ is a group having the structure

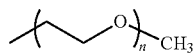

wherein n is 4; and the nanocapsule has a diameter of 1 to 100 nanometers.

Embodiment 22

The nanocapsule of any of embodiments 2 to 21, wherein the nanocapsule comprises 1 to 10 weight percent, based on the weight of the nanocapsule, of the core comprising 85 to 99.99 weight percent, based on the weight of the core, of carvacrol oil; and 0.01 to 15 weight percent, based on the weight of the core, of the hydrophobic anhydride containing polymer comprising repeating units of Formula (VII) wherein m is an integer from 1 to 16; and 90 to 99 weight percent, based on the weight of the nanocapsule, of the shell comprising the copolymer, wherein each occurrence of X is —O—; each occurrence of $L^1$ and $L^2$ are propylene; each occurrence of $R^1$ is hydrogen; each occurrence of y is 3; each occurrence of p is 1; each occurrence of $R^2$ is a group having the structure

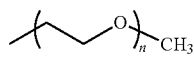

wherein n is 4; each occurrence of $R^3$ is hydrogen; each occurrence of a is 3; each occurrence of b is 1; the nanocapsule has a diameter of 1 to 100 nanometers; and wherein at least a portion of the shell is crosslinked with the anhydride-containing polymer.

Embodiment 23

The nanocapsule of any of embodiments 1 to 22, wherein the copolymer further comprises a degradable repeating unit having a formula selected from repeating units of formula (IV).

Embodiment 24

The nanocapsule of embodiment 23, wherein the degradable repeating unit is present in an amount of 5 to 95 mole percent, preferably 10 to 50 mole percent, based on the total moles of the copolymer.

Embodiment 25

A dispersion comprising a plurality of nanocapsules according to any of embodiments 1 to 24.

Embodiment 26

The dispersion of embodiment 25, wherein the nanocapsules are dispersed in an aqueous solution.

Embodiment 27

A method of treating a bacterial biofilm, the method comprising, contacting the dispersion of embodiments 25 or 26 with a bacterial biofilm.

Embodiment 28

The method of embodiment 27, wherein the bacterial biofilm comprises *Escherichia coli*, *Pseudomonas* bacteria, Staphylococcal bacteria, Enterobacteriaceae bacteria, *Streptococcus* bacteria, *Haemophilus influenzae*, *Leptospira interrogans*, *Legionella* bacteria, or a combination thereof.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety, including priority U.S. Patent Application No. 62/213,779, filed Sep. 3, 2015. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. "Combination" is inclusive of blends, mixtures, alloys, reaction products, and the like. "Or" means "and/or". Further, it should further be noted that the terms "first," "second," and the like herein do not denote any order, quantity, or importance, but rather are used to distinguish one element from another.

As used herein, the term "alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene (—$CH_2$—) or propylene (—$(CH_2)_3$—)). "Aryl" means a monovalent, monocyclic or polycyclic aromatic group (e.g., phenyl or naphthyl). Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Groups that can be present on a substituted position include (—$NO_2$), cyano (—CN), hydroxy (—OH), halogen, thiol (—SH), thiocyano (—SCN), $C_{2-6}$ alkanoyl (e.g., acyl (H₃CC(=O)—); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy; $C_{0-10}$ aryloxy such as phenoxy; $C_{1-6}$ alkylthio; $C_{1-6}$ or $C_{1-3}$ alkylsulfinyl; C1-6 or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 1 to 3 separate or fused rings and from 6 to 18 ring carbon atoms.

The invention claimed is:
1. A nanocapsule comprising,
a liquid hydrophobic core comprising an essential oil; and
a shell encapsulating the core, the shell comprising a copolymer comprising repeating units of Formula (I) and (II)

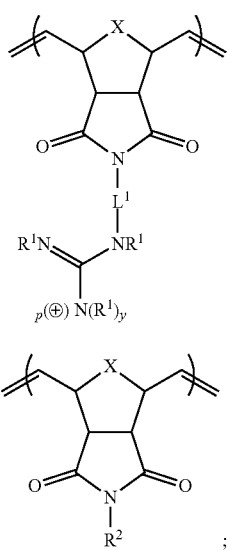

wherein
X is independently at each occurrence —O—, —S—, —CH₂—, —(CR⁴R⁵)—, or

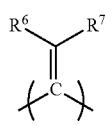

wherein R⁴ and R⁵ are independently at each occurrence a $C_{1-6}$ alkyl group and R⁶ and R⁷ are independently at each occurrence hydrogen or a $C_{1-6}$ alkyl group;
L¹ is independently at each occurrence a divalent group that is (—CH₂—)$_z$, wherein z is an integer from 1 to 10, a divalent a $C_{1-20}$ alkylene oxide group, or a divalent poly($C_{1-6}$ alkylene oxide) group;
R¹ is independently at each occurrence hydrogen, a $C_{1-12}$ alkylene group, or a —C(=O)—O—($C_{1-6}$ alkyl) group;
y is 2 or 3;
p is 0 or 1; and R² is independently at each occurrence a $C_{1-12}$ alkylene group, a $C_{6-20}$ arylene group, a $C_{1-20}$ alkylene oxide group, a poly($C_{1-6}$ alkylene oxide) group, or a zwitterionic group.
2. The nanocapsule of claim 1, wherein the copolymer further comprises repeating units of Formula (III)

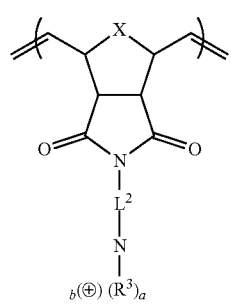

wherein
X is independently at each occurrence —O—, —S—, —CH₂—, —(CR⁴R⁵)—, or

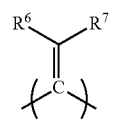

wherein R⁴ and R⁵ are independently at each occurrence a $C_{1-6}$ alkyl group and R⁶ and R⁷ are independently at each occurrence hydrogen or a $C_{1-6}$ alkyl group;
L² is independently at each occurrence a divalent group that is (—CH₂—)$_z$, wherein z is an integer from 1 to 10, a divalent a $C_{1-20}$ alkylene oxide group, or a divalent poly($C_{1-6}$ alkylene oxide) group;
R³ is independently at each occurrence hydrogen, a $C_{1-12}$ alkylene group, or a —C(=O)—O—($C_{1-6}$ alkyl) group;
a is 2 or 3; and
b is 0 or 1.
3. The nanocapsule of claim 1, wherein the copolymer further comprises repeating units of Formula (IV).
4. The nanocapsule of claim 1, wherein the copolymer further comprises repeating units of Formula (V)

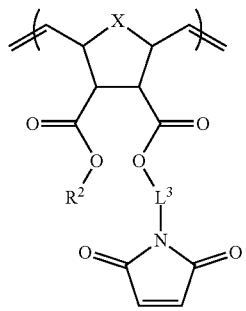

wherein X is independently at each occurrence —O—, —S—, —CH₂—, —(CR⁴R⁵)—, or

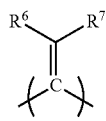

wherein $R^4$ and $R^5$ are independently at each occurrence a $C_{1-6}$ alkyl group and $R^6$ and $R^7$ are independently at each occurrence hydrogen or a $C_{1-6}$ alkyl group;

$R^2$ is independently at each occurrence a $C_{1-12}$ alkylene group, a $C_{6-20}$ arylene group, a $C_{1-20}$ alkylene oxide group, a poly($C_{1-6}$ alkylene oxide) group, or a zwitterionic group; and $L^3$ is a divalent group that is $(-CH_2-)_z$, wherein z is an integer from 1 to 10.

5. The nanocapsule of claim 1, wherein the core further comprises a hydrophobic anhydride-containing polymer in an amount of 0.01 to 15 weight percent, based on the weight of the core, wherein the hydrophobic anhydride-containing polymer comprising repeating units of Formula (VI)

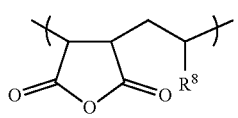
(VI)

wherein $R^8$ is independently at each occurrence a hydrogen, a $C_{1-20}$ alkyl group or a $C_{6-20}$ aryl group.

6. The nanocapsule of claim 5, wherein at least a portion of the shell is crosslinked with the anhydride-containing polymer.

7. The nanocapsule of claim 1, wherein the essential oil is selected from the group consisting of peppermint oil, oregano oil, thymol, menthol, methyl salicylate, eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, lemon oil, orange oil, sage oil, rosemary oil, cinnamon oil, pimento oil, laurel oil, cedar leaf oil, clove oil, cilantro oil, coriander oil, or a combination thereof.

8. The nanocapsule of claim 2, wherein the copolymer comprises
5 to 50 mole percent repeating units of Formula (I);
10 to 50 mole percent repeating units of Formula (II); and
25 to 45 mole percent repeating units of Formula (III);
wherein mole percent of each component is based on the total moles of the copolymer.

9. The nanocapsule of claim 1, wherein
X is —O—;
$L^1$ is propylene;
$R^1$ is hydrogen;
y is 3;
p is 1; and
$R^2$ is a $C_{1-20}$ alkylene oxide group.

10. The nanocapsule of claim 1, wherein $R^2$ is a group having the structure

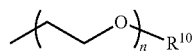

wherein
n is 1, 2, 3, or 4; and
$R^{10}$ is hydrogen, methyl, or a $C_{1-6}$ alkylamino group.

11. The nanocapsule of claim 2, wherein
$R^3$ is hydrogen;
$L^2$ is propylene;
a is 3; and
b is 1.

12. The nanocapsule of claim 1, wherein the copolymer has a number average molecular weight of 3,000 to 100,000 Daltons.

13. The nanocapsule of claim 1, comprising
90 to 99.9 weight percent of the core; and
0.1 to 10 weight percent of the shell;
wherein weight percent is based on the total weight of the nanocapsule.

14. The nanocapsule of claim 1, wherein the nanocapsule comprises
1 to 10 weight percent, based on the weight of the nanocapsule, of the core comprising carvacrol oil; and
90 to 99 weight percent, based on the weight of the nanocapsule, of the shell comprising the copolymer, wherein
each occurrence of X is —O—;
each occurrence of $L^1$ is propylene;
each occurrence of $R^1$ is hydrogen;
each occurrence of y is 3;
each occurrence of p is 1;
each occurrence of $R^2$ is a group having the structure

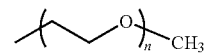

wherein n is 4; and
the nanocapsule has a diameter of 1 to 100 nanometers.

15. The nanocapsule of claim 2, wherein the nanocapsule comprises
1 to 10 weight percent, based on the weight of the nanocapsule, of the core comprising
85 to 99.99 weight percent, based on the weight of the core, of carvacrol oil; and
0.01 to 15 weight percent, based on the weight of the core, of the hydrophobic anhydride containing polymer comprising repeating units of Formula (VI)

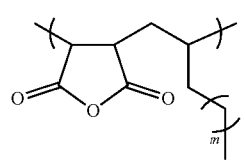
(VI)

wherein m is an integer from 1 to 16; and
90 to 99 weight percent, based on the weight of the nanocapsule, of the shell comprising the copolymer, wherein
each occurrence of X is —O—;
each occurrence of $L^1$ and $L^2$ are propylene;
each occurrence of $R^1$ is hydrogen;

each occurrence of y is 3;
each occurrence of p is 1;
each occurrence of R² is a group having the structure

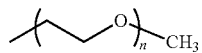

wherein n is 4;
each occurrence of R³ is hydrogen;
each occurrence of a is 3;
each occurrence of b is 1;
the nanocapsule has a diameter of 1 to 100 nanometers; and
wherein at least a portion of the shell is crosslinked with the anhydride-containing polymer.

16. A dispersion comprising a plurality of nanocapsules according to claim 1.

17. The dispersion of claim 16, wherein the nanocapsules are dispersed in an aqueous solution.

18. A method of treating a bacterial biofilm, the method comprising,
contacting the dispersion of claim 16 with a bacterial biofilm.

19. The method of claim 18, wherein the bacterial biofilm comprises *Escherichia coli, Pseudomonas* bacteria, Staphylococcal bacteria, Enterobacteriaceae bacteria, *Streptococcus* bacteria, *Haemophilus influenzae, Leptospira interrogans, Legionella* bacteria, or a combination thereof.

* * * * *